US012111430B2

(12) United States Patent
Horiuchi et al.

(10) Patent No.: US 12,111,430 B2
(45) Date of Patent: Oct. 8, 2024

(54) RADIATION DETECTOR AND RADIOGRAPHY APPARATUS

(71) Applicant: FUJIFILM CORPORATION, Tokyo (JP)

(72) Inventors: Hisatsugu Horiuchi, Kanagawa (JP); Sho Shimizukawa, Kanagawa (JP); Munetaka Kato, Kanagawa (JP); Tatsuya Taneichi, Kanagawa (JP); Naoyuki Nishino, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 276 days.

(21) Appl. No.: 17/807,859

(22) Filed: Jun. 20, 2022

(65) Prior Publication Data

US 2023/0015140 A1    Jan. 19, 2023

(30) Foreign Application Priority Data

Jul. 19, 2021    (JP) .................................. 2021-118904

(51) Int. Cl.
| | |
|---|---|
| *G01T 1/24* | (2006.01) |
| *A61B 6/00* | (2024.01) |
| *A61B 6/03* | (2006.01) |
| *A61B 6/40* | (2024.01) |
| *G01N 23/046* | (2018.01) |
| *G01T 1/20* | (2006.01) |

(52) U.S. Cl.
CPC ................ *G01T 1/244* (2013.01); *G01T 1/24* (2013.01); *A61B 6/032* (2013.01); *A61B 6/4085* (2013.01); *A61B 6/4435* (2013.01); *G01N 23/046* (2013.01); *G01N 2223/419* (2013.01); *G01T 1/2018* (2013.01); *G01T 1/20188* (2020.05)

(58) Field of Classification Search
CPC ....... G01T 1/244; G01T 1/24; G01T 1/20188; G01T 1/2018
See application file for complete search history.

(56) References Cited

U.S. PATENT DOCUMENTS

2003/0031296 A1* 2/2003 Hoheisel ............. G01T 1/20188
378/98.8
2004/0238750 A1 12/2004 Vafi et al.
(Continued)

FOREIGN PATENT DOCUMENTS

JP    2004-361402 A    12/2004

*Primary Examiner* — Chih-Cheng Kao
(74) *Attorney, Agent, or Firm* — SOLARIS Intellectual Property Group, PLLC

(57) ABSTRACT

A radiation detector includes a support table in which an attachment surface having an arc surface shape is formed, a sensor panel which has a rectangular plate shape and in which pixels that include TFTs and detect radiation are two-dimensionally arranged, a circuit board, a flexible cable, and a reduction structure. The sensor panel is attached to the attachment surface while being curved following the arc surface shape. The flexible cables connect a curved side of the sensor panel and a reading circuit board and are arranged along the curved side. The flexible cable is bent to dispose the reading circuit board at an angle of 90° with respect to the sensor panel. The reduction structure reduces a bias of a stretching force applied to the flexible cable caused by the curved side.

28 Claims, 32 Drawing Sheets

(56) References Cited

U.S. PATENT DOCUMENTS

| | | | |
|---|---|---|---|
| 2006/0200976 A1* | 9/2006 | Freund | H01R 13/6485 |
| | | | 29/825 |
| 2007/0206721 A1* | 9/2007 | Tkaczyk | G01T 1/249 |
| | | | 378/19 |
| 2013/0306877 A1* | 11/2013 | Pohan | G01T 1/2985 |
| | | | 250/394 |
| 2018/0275292 A1* | 9/2018 | Akamatsu | H04N 5/32 |

* cited by examiner

FIG. 15

IRRADIATION CONDITION TABLE 141

| IMAGING PROCEDURE | | | IRRADIATION CONDITIONS (TUBE VOLTAGE  TUBE CURRENT  IRRADIATION TIME) | | | ... |
|---|---|---|---|---|---|---|
| STANDING POSTURE | HEAD | ADULT MALE | 100KV | 10mA | 0.5ms | ... |
| STANDING POSTURE | HEAD | ADULT FEMALE | 100KV | 10mA | 0.5ms | ... |
| STANDING POSTURE | NECK | ADULT MALE | 80KV | 8mA | 0.5ms | ... |
| ... | | | | | | |
| SITTING POSTURE | SPINE | ADULT MALE | 120KV | 12mA | 0.5ms | ... |
| SITTING POSTURE | SPINE | ADULT FEMALE | 120KV | 12mA | 0.5ms | ... |
| ... | | | | | | |

156

RADIATION DETECTOR AND RADIOGRAPHY APPARATUS

CROSS-REFERENCE TO RELATED APPLICATIONS

The present application claims priority under 35 U.S.C. § 119 to Japanese Patent Application No. 2021-118904, filed on Jul. 19, 2021. The above application is hereby expressly incorporated by reference, in its entirety, into the present application.

BACKGROUND

1. Technical Field

The technology of the present disclosure relates to a radiation detector and a radiography apparatus.

2. Description of the Related Art

A radiation detector is known which detects radiation transmitted through a subject and outputs a radiographic image of the subject. The radiation detector is provided with an imaging sensor having a rectangular plate shape. The imaging sensor has pixels. The pixels sense the radiation or visible light converted from the radiation and generate charge. A radiographic image is obtained by reading out the charge from the pixels and performing various types of signal processing.

Examples of an imaging sensor include a complementary metal oxide semiconductor (CMOS) solid-state imaging element and a sensor panel using a thin film transistor (hereinafter, abbreviated to a TFT). The sensor panel can have a larger area and a higher resolution than the CMOS solid-state imaging element. Therefore, it is advantageous to use the sensor panel.

JP2004-361402A discloses a radiation detector using a sensor panel. In JP2004-361402A, the sensor panel is curved in a curved surface shape, and the irradiation distance of radiation from a radiation source is substantially the same on the entire surface of the sensor panel to eliminate the distortion of a radiographic image.

In JP2004-361402A, the sensor panel is attached to a support table. An attachment surface to which the sensor panel is attached following the curved surface shape is formed in the support table. A margin portion is provided in the attachment surface along two orthogonal sides of the sensor panel. Then, two circuit boards having a rectangular plate shape are attached to the margin portion. The circuit board is attached such that a surface on which an electric component is mounted is substantially parallel to an imaging surface of the sensor panel. The circuit board is connected to the side of the sensor panel through a plurality of flexible cables.

SUMMARY

Of course, since no pixels are provided in the margin portion, the margin portion does not contribute to capturing a radiographic image. For this reason, it is better that there is no margin portion from the viewpoint of reducing the size of the radiation detector. Therefore, a method is considered which attaches a sensor panel to an attachment surface of a support table, bends a flexible cable, and disposes a circuit board at an angle of, for example, 90° with respect to the sensor panel, thereby disposing the circuit board without providing a margin portion. However, since the side of the sensor panel to which the flexible cable is connected is curved, an excessive stretching force may be applied to the flexible cable depending on the location. As a result, there is a concern that defects, such as cracks and malfunction, will occur in the circuit board.

One embodiment according to the technology of the present disclosure provides a radiation detector and a radiography apparatus that can reduce a concern that a defect will occur in a circuit board.

According to an aspect of the present disclosure, there is provided a radiation detector comprising: a support table in which an attachment surface having a curved surface shape is formed; a sensor panel which has a rectangular plate shape and is attached to the attachment surface while being curved following the curved surface shape and in which pixels that include thin film transistors and detect radiation are two-dimensionally arranged; a circuit board; a plurality of flexible cables that connect a curved side of the sensor panel and the circuit board, are arranged along the curved side, and are bent to dispose the circuit board at a set angle with respect to the sensor panel; and a reduction structure that reduces a bias of a stretching force applied to the plurality of flexible cables caused by the curved side.

Preferably, the circuit board has a rectangular plate shape, and the reduction structure is configured by the flexible cables that have a length corresponding to a distance between the circuit board and the curved side.

Preferably, the flexible cable has one end thermally compressed to the curved side before being curved and the other end thermally compressed to the circuit board.

Preferably, the flexible cables disposed at positions that are symmetric with respect to a center line of the circuit board have the same length.

Preferably, an integrated circuit is mounted on the flexible cable.

Preferably, a length from the sensor panel to the integrated circuit in the plurality of flexible cables is the length corresponding to the distance between the circuit board and the curved side, and lengths from the integrated circuits in the plurality of flexible cables to the circuit board are the same.

Preferably, a minimum value of the length from the sensor panel to the integrated circuit of the flexible cable is a minimum length of a wiring line that connects the sensor panel and the integrated circuit, and a maximum value of the length from the sensor panel to the integrated circuit of the flexible cable is a length obtained by adding a difference between a longest distance and a shortest distance among the distances between the circuit board and the curved side to the minimum length of the wiring line connecting the sensor panel and the integrated circuit.

Preferably, the integrated circuits have the same performance.

Preferably, the circuit board is a reading circuit board for reading out charge accumulated in the pixel, and the integrated circuit includes an analog/digital converter that converts an analog signal indicated by the charge into a digital signal.

Preferably, the circuit board is a switching circuit board for giving an on/off signal to the thin film transistor, and the integrated circuit includes a gate driver that emits the on/off signal.

Preferably, each of the plurality of flexible cables is divided into a first flexible cable having one end connected to the curved side and a second flexible cable having one end connected to the circuit board. Preferably, in the plurality of flexible cables, the first flexible cables have the same length, and the radiation detector further comprises a relay board to which the other end of the first flexible cable and the other end of the second flexible cable are connected and which is disposed between the sensor panel and the circuit board.

Preferably, the reduction structure is configured by the second flexible cables having a length corresponding to a distance between the circuit board and the curved side.

Preferably, the second flexible cables disposed at positions that are symmetric with respect to a center line of the circuit board have the same length.

Preferably, in the plurality of flexible cables, the second flexible cables have the same length, and the reduction structure is configured by the circuit board to which one end of the second flexible cable is connected and which has a curved end portion having a shape following the curved side.

Preferably, the first flexible cable has the one end thermally compressed to the curved side and the other end thermally compressed to the relay board, the relay board has a connector to which the other end of the second flexible cable is connected, and the circuit board has a connector to which the one end of the second flexible cable is connected.

Preferably, an integrated circuit is mounted on the first flexible cable or the relay board.

Preferably, the circuit board is a reading circuit board for reading out charge accumulated in the pixel, and the integrated circuit includes an analog/digital converter that converts an analog signal indicated by the charge into a digital signal.

Preferably, the circuit board is a switching circuit board for giving an on/off signal to the thin film transistor, and the integrated circuit includes a gate driver that emits the on/off signal.

Preferably, the reduction structure is configured by the circuit board that is curved following the curved surface shape.

Preferably, the reduction structure is configured by divided circuit boards and an inter-board connection flexible cable that connects adjacent circuit boards among the divided circuit boards.

Preferably, the circuit board is a reading circuit board for reading out charge accumulated in the pixel and includes a first reading circuit board that takes charge of reading out the charge in a region which is half of the sensor panel and a second reading circuit board that takes charge of reading out the charge in a region which is the other half of the sensor panel, and the first reading circuit board and the second reading circuit board are connected to two opposite curved sides of the sensor panel through the flexible cables.

Preferably, the sensor panel includes two sensor panels of a first sensor panel and a second sensor panel, and the first sensor panel and the second sensor panel are arranged such that end portions on sides other than the curved side to which the circuit board is connected overlap each other in a thickness direction.

Preferably, the circuit board connected to the first sensor panel and the circuit board connected to the second sensor panel are disposed at positions that have a two-fold symmetrical relationship.

According to another aspect of the present disclosure, there is provided a radiography apparatus comprising the above-described radiation detector and a radiation source that emits the radiation.

Preferably, the radiography apparatus further comprises: an annular frame to which the radiation detector and the radiation source are attached and in which a subject is positioned in a cavity; and a rotation mechanism that rotates the frame around the subject to capture radiographic images of the subject at different angles. Preferably, the attachment surface has an arc surface shape following the annular frame.

Preferably, the radiography apparatus is a computed tomography apparatus that obtains a tomographic image of the subject on the basis of the radiographic images captured at different angles.

Preferably, the radiation source emits the radiation having a conical shape.

Preferably, the subject is positioned in the cavity in either a standing posture or a sitting posture.

According to the technology of the present disclosure, it is possible to provide a radiation detector and a radiography apparatus that can reduce a concern that a defect will occur in a circuit board.

BRIEF DESCRIPTION OF THE DRAWINGS

Exemplary embodiments according to the technique of the present disclosure will be described in detail based on the following figures, wherein:

FIG. 15 is a diagram illustrating an irradiation condition table;

DETAILED DESCRIPTION

First Embodiment

Figure 1:
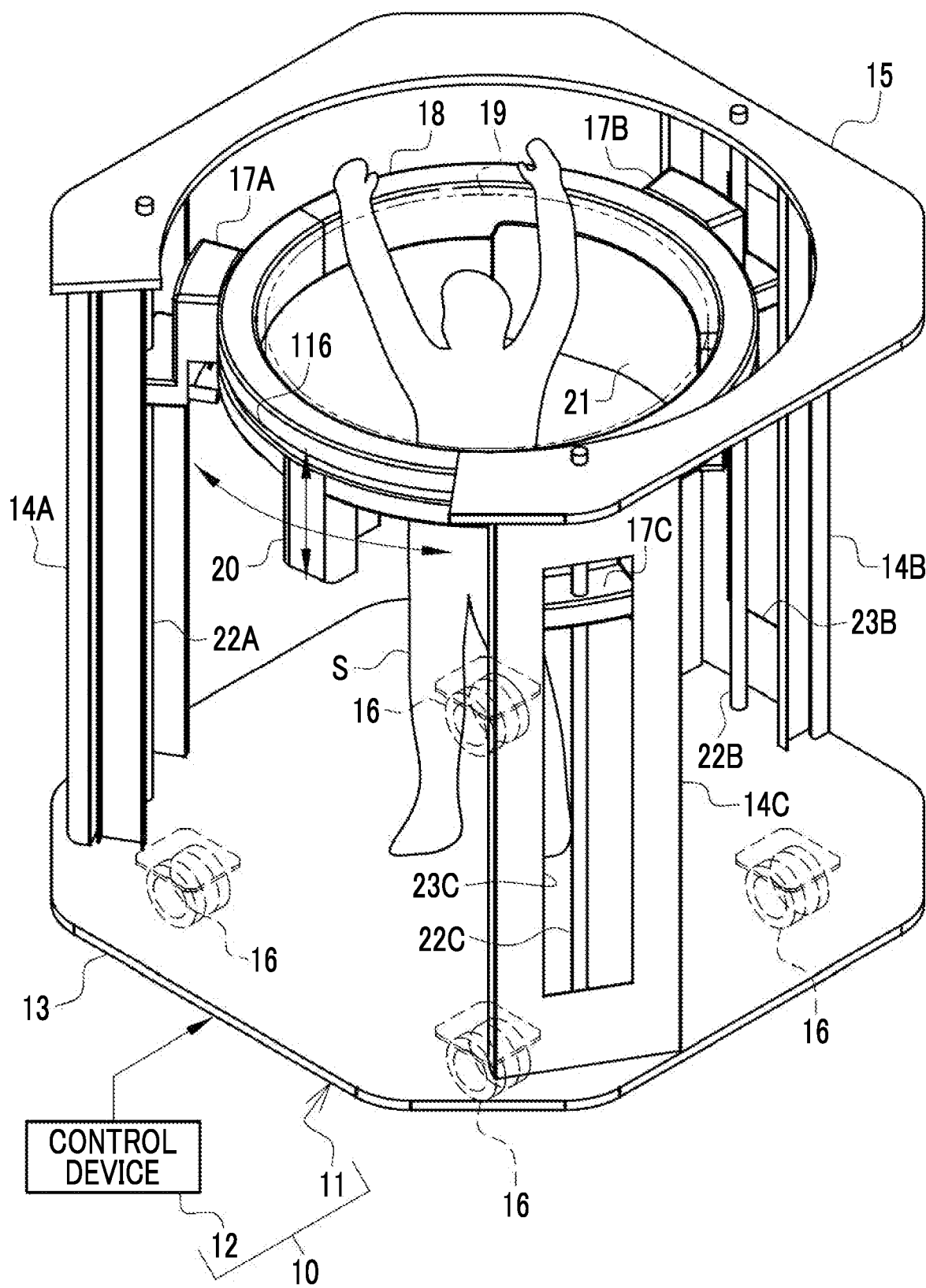
FIG. 1 is a perspective view illustrating a CT apparatus.
Figure 2:
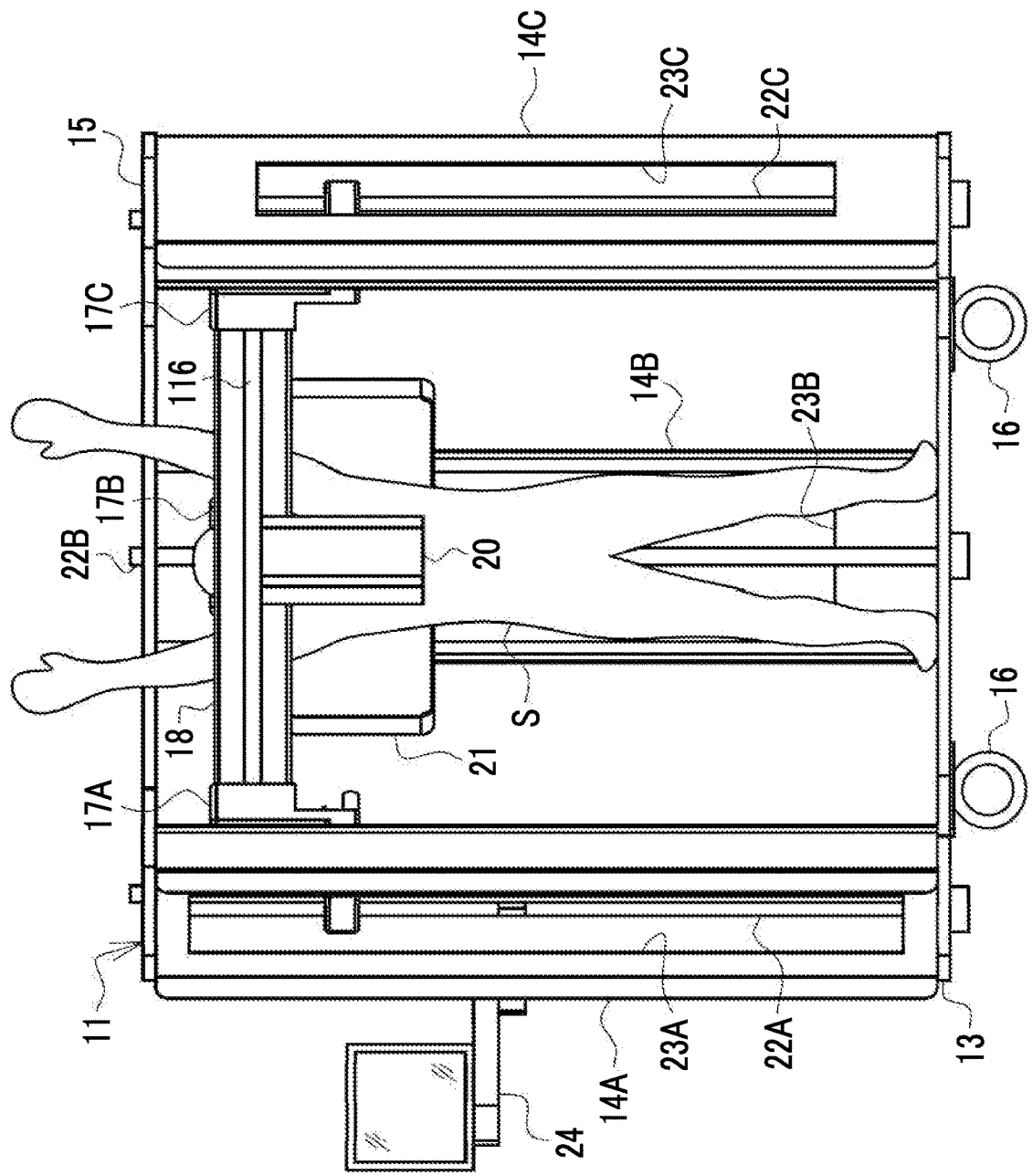
FIG. 2 is a front view illustrating an apparatus main body of the CT apparatus.
Figure 3:
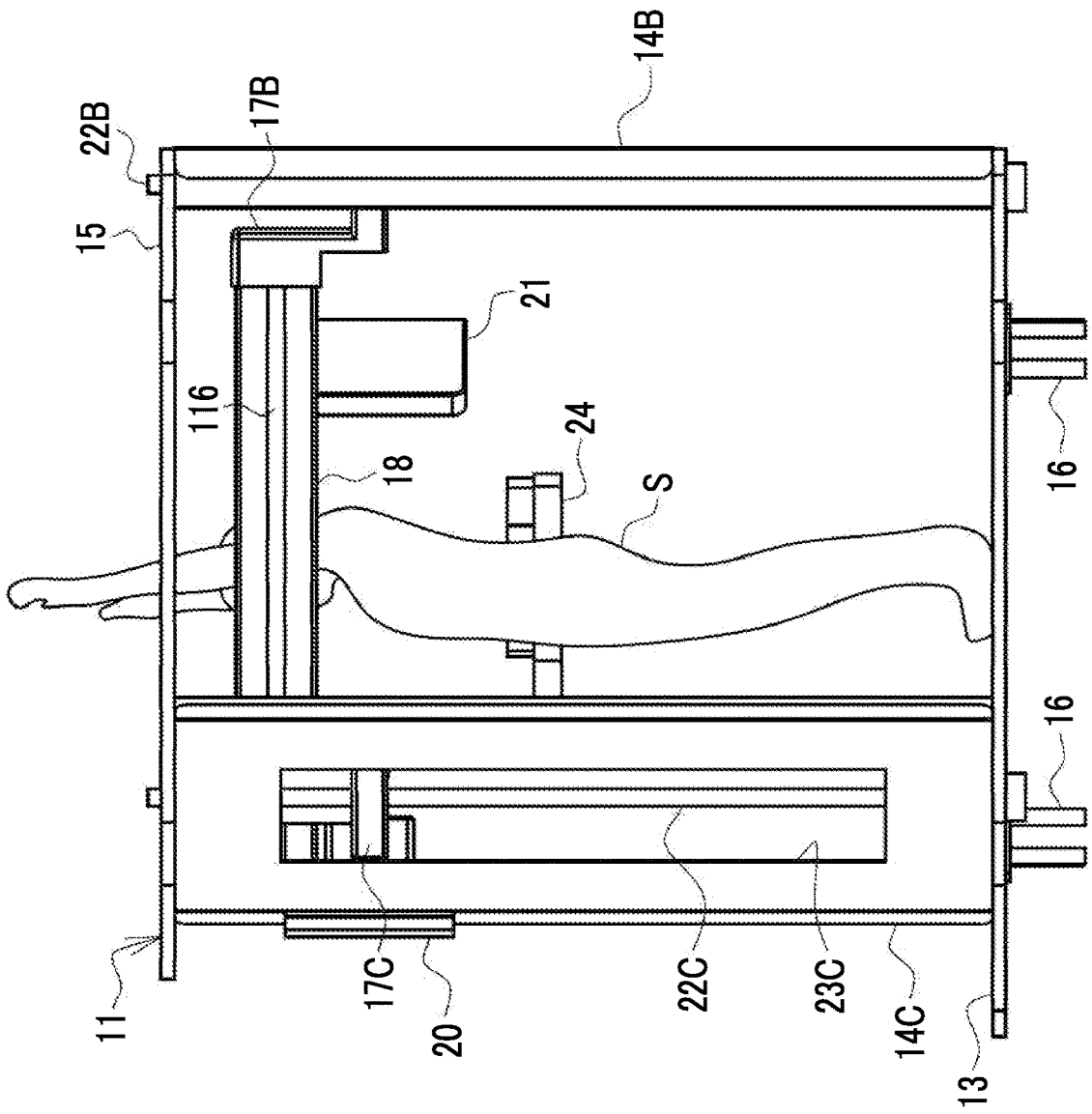
FIG. 3 is a side view illustrating the apparatus main body of the CT apparatus.

For example, as illustrated in FIG. 1, a CT apparatus 10 is an apparatus for obtaining a tomographic image TI (see FIG. 17) of a subject S and includes an apparatus main body 11 and a control device 12. The apparatus main body 11 is installed, for example, in a radiography room of a medical facility. The control device 12 is installed, for example, in a control room next to the radiography room. The control device 12 is a desktop personal computer, a notebook personal computer, or a tablet terminal. The CT apparatus 10 is an example of a "radiography apparatus" according to the technology of the present disclosure.

For example, as illustrated in FIGS. 1 to 4, the apparatus main body 11 comprises a stage 13, three columns 14A, 14B, and 14C, and a top plate 15. The stage 13 is an octagonal flat surface. Casters 16 for transportation are attached to four corners of a rear surface of the stage 13.

The caster 16 comprises a rotation lock mechanism (not illustrated). After the apparatus main body 11 is installed at an installation position, the rotation lock mechanism can be operated to lock the rotation of the caster 16. Alternatively, the caster 16 can be removed from the stage 13. The caster 16 can be removed after the apparatus main body 11 is installed at the installation position.

The outer shape of the columns 14A to 14C is a rectangular plate shape, and the columns 14A to 14C are vertically provided at four corners of the surface of the stage 13. The columns 14A and 14C are disposed on the front left and right sides of the apparatus main body 11 (the front left and right sides of the subject S). The column 14B is disposed at the center of the rear side of the apparatus main body 11 (behind the subject S). The top plate 15 is attached to the upper end portions of the columns 14A to 14C. The top plate 15 is an octagonal flat surface having an outer shape following the stage 13. The top plate 15 has a C-shape in which a central portion is hollowed out in a circular shape and a portion corresponding to the front side of the apparatus main body 11 between the columns 14A and 14C is cut out. Further, in the following description, the columns 14A to 14C are collectively referred to as columns 14 in a case in which they do not need to be distinguished from each other.

A connection member 17A is connected to the column 14A, a connection member 17B is connected to the column 14B, and a connection member 17C is connected to the column 14C. A frame 18 is connected to the connection members 17A to 17C. That is, the columns 14A to 14C and the frame 18 are connected to each other through the connection members 17A to 17C. Furthermore, in the following description, the connection members 17A to 17C are collectively referred to as connection members 17 in a case in which they do not need to be distinguished from each other.

The frame 18 has an annular shape. The subject S is positioned at a center C (see FIG. 4) of a cavity 19 of the annular frame 18. FIGS. 1 to 4 illustrate an aspect in which the subject S in a standing posture with both hands raised above the head is positioned.

The column 14 is provided with a guide rail (not illustrated) to which the connection member 17 is fitted. The connection member 17 and thus the frame 18 can be moved up and down in the vertical direction along the guide rail. That is, the columns 14 hold the frame 18 so as to be movable up and down in the vertical direction. In addition, the frame 18 can be rotated around the subject S using the center C as a central axis. That is, the columns 14A to 14C hold the frame 18 so as to be rotatable around the subject S. Further, the height position of the frame 18 may be changed by expanding and contracting the columns 14.

A radiation source 20 that emits radiation R (see FIG. 6), such as X-rays or γ-rays, and a radiation detector 21 that detects the radiation R are attached to the frame 18. Both the radiation source 20 and the radiation detector 21 protrude from a lower edge of the frame 18. The radiation source 20 and the radiation detector 21 are disposed at opposite positions (positions that are 180° away from each other) of the frame 18. The radiation source 20 has a box shape, and the radiation detector 21 has a pad shape. In a plan view of the frame 18 or the like from above, the radiation detector 21 has an arc surface shape that is convex toward the opposite side of the radiation source 20 and follows the shape of the frame 18.

The column 14A is provided with a screw shaft 22A, the column 14B is provided with a screw shaft 22B, and the column 14C is provided with a screw shaft 22C. The screw shafts 22A to 22C have a height from the stage 13 to the top plate 15. The screw shafts 22A to 22C are rotated such that the connection members 17A to 17C and thus the frame 18 are moved up and down in the vertical direction. In addition, in the following description, the screw shafts 22A to 22C are collectively referred to as screw shafts 22 in a case in which they do not need to be distinguished from each other.

The column 14A has an opening 23A, the column 14B has an opening 23B, and the column 14C has an opening 23C. The openings 23A to 23C are formed by hollowing out most of the columns 14A to 14C in a rectangular shape, respectively. The subject S can be visually recognized from the outside of the apparatus main body 11 through the openings 23A to 23C. Each of the columns 14A to 14C partially looks like two columns because of each of the openings 23A to 23C. However, since the column is connected at the top and bottom of each of the openings 23A to 23C, the number is columns is one.

A touch panel display 25 is attached to the column 14A through a movable arm 24. The touch panel display 25 is operated by an operator. Further, the touch panel display 25 displays various kinds of information to the operator.

Figure 4:
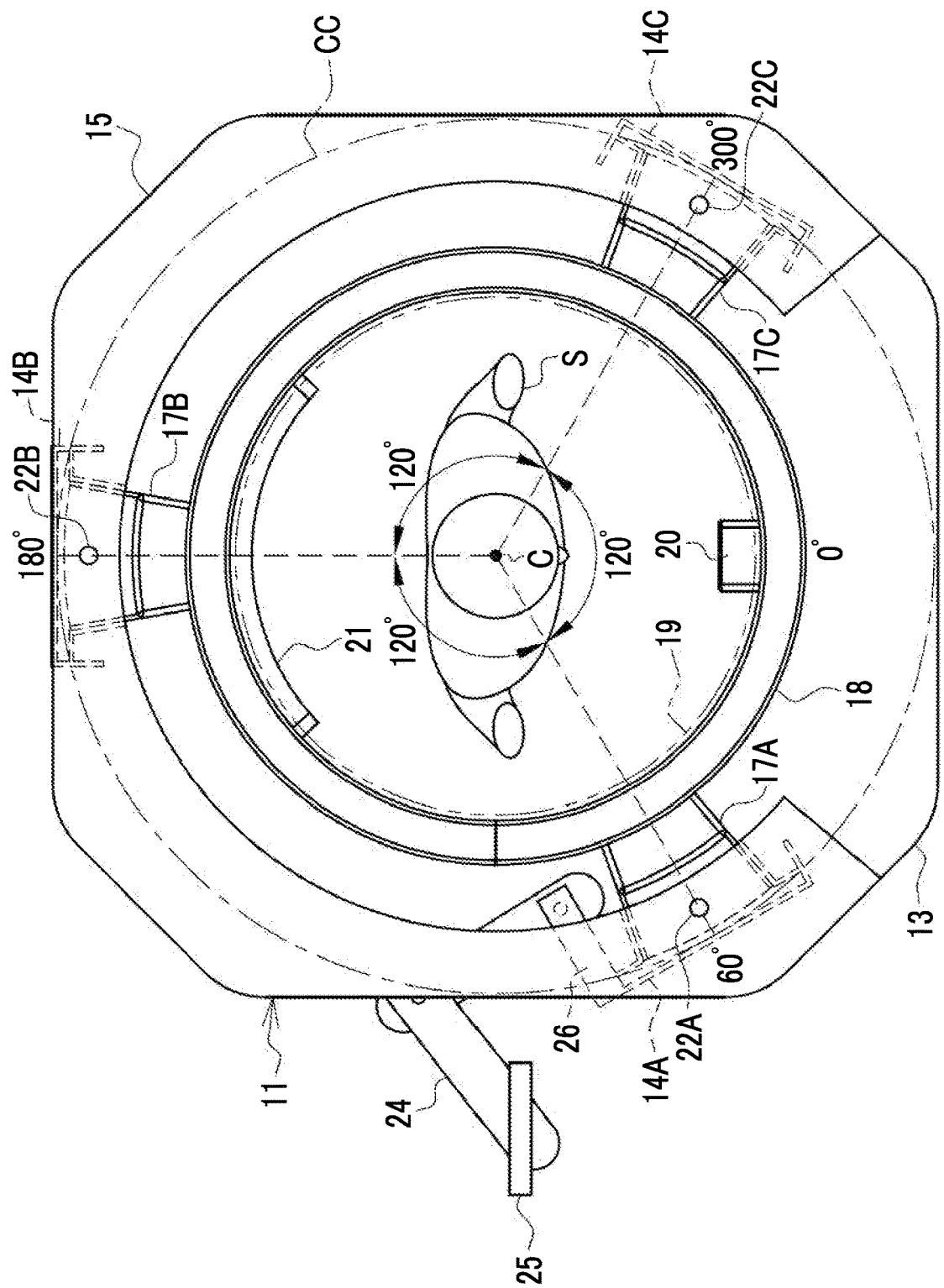
FIG. 4 is a top view illustrating the apparatus main body of the CT apparatus.

In FIG. 4 which is a plan view of the frame 18 and the like from above, in a case in which the position where the radiation source 20 is located in front of the apparatus main body 11 is set as a position of 0°, the column 14A is disposed at a position of 60° on a circle CC having the center C of the frame 18 as its center, the column 14B is disposed at a position of 180° on the circle CC, and the column 14C is disposed at a position of 300° on the circle CC. That is, the columns 14A to 14C are disposed at intervals of 120° on the circle CC. In addition, angles, such as "0°" and "60°", indicate, for example, "0°" and "60°" including an error (for example, an error of about 1% to 10%) that is generally allowed in the technical field to which the technology of the present disclosure belongs and does not depart from the gist of the technology of the present disclosure, in addition to perfect "0°" and "60°". Further, the term "equal interval" indicates an "equal interval" including an error (for example, an error of about 1% to 10%) that is generally allowed in the technical field to which the technology of the present disclosure belongs and does not depart from the gist of the technology of the present disclosure, in addition to a perfect "equal interval".

Figure 5:
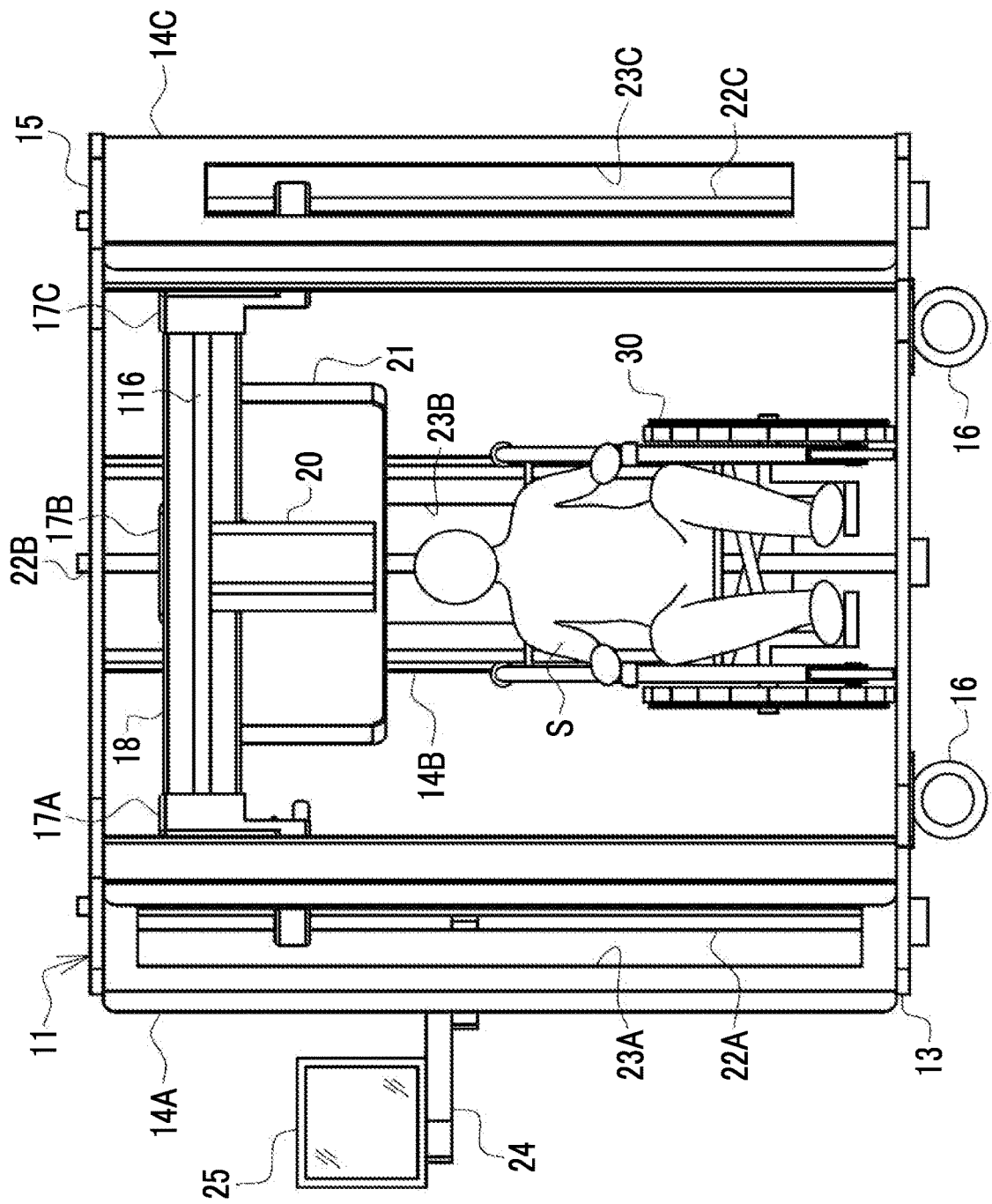
FIG. 5 is a front view illustrating the apparatus main body of the CT apparatus in a state in which a subject in a sitting posture on a wheelchair is positioned.

FIGS. 1 to 4 illustrate an example in which the subject S in a standing posture with both hands raised above the head is positioned in the cavity 19. However, the present disclosure is not limited to thereto. For example, as illustrated in FIG. 5, the CT apparatus 10 can image the subject S who is positioned in the cavity 19 in a sitting posture on a wheelchair 30. In addition, both the subject S in the standing posture and the subject S in the sitting posture on the wheelchair 30 are positioned so as to face the front at the position of 0°.

Figure 6:
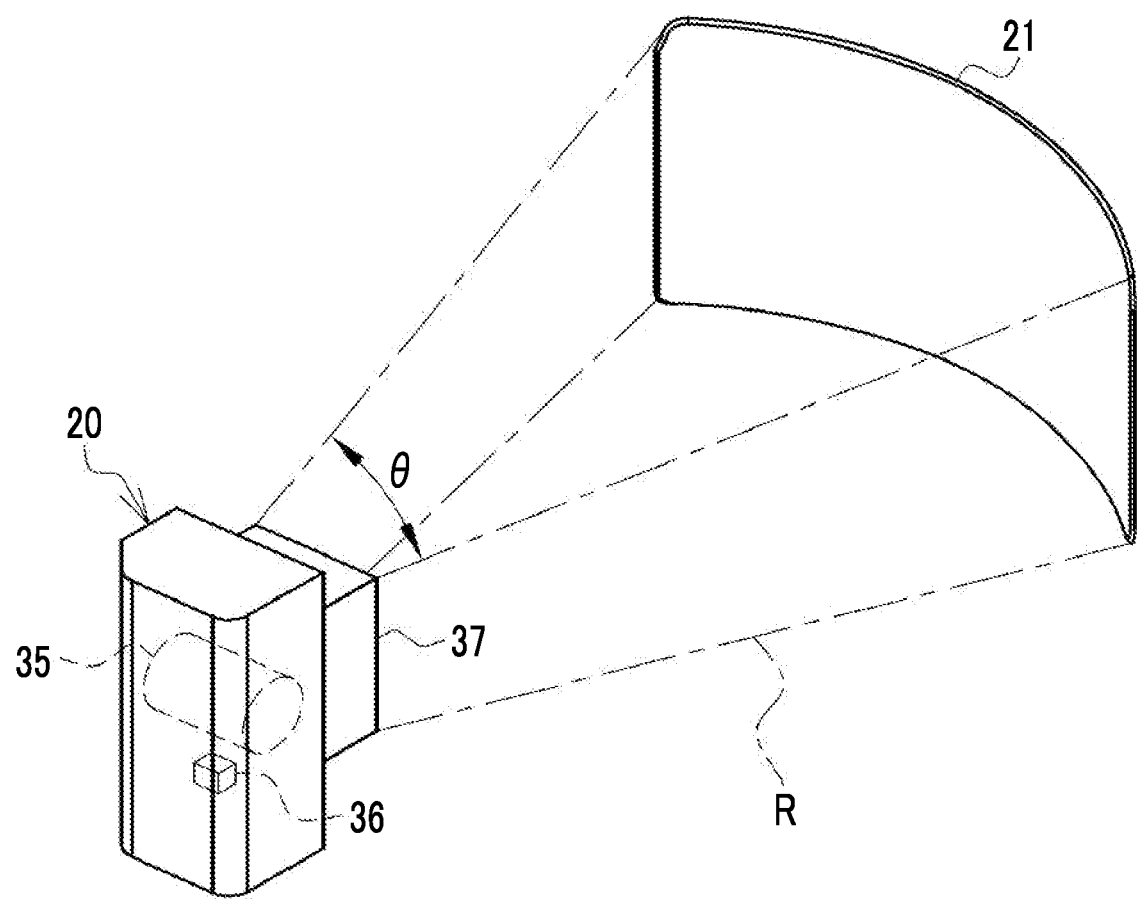
FIG. 6 is a perspective view illustrating a radiation source, a radiation detector, and radiation.

For example, as illustrated in FIG. 6, the radiation source 20 includes a radiation tube 35 and an irradiation field lamp 36. The radiation tube 35 emits the radiation R. The irradiation field lamp 36 emits, for example, orange visible light indicating the irradiation field of the radiation R.

Further, the radiation source 20 includes an irradiation field limiter 37. The irradiation field limiter 37 is also called a collimator and defines the irradiation field of the radiation R to the radiation detector 21. An incident opening through which the radiation R from the radiation tube 35 is incident and an exit opening through which the radiation R exits are formed in the irradiation field limiter 37. For example, four shielding plates are provided in the vicinity of the exit opening. The shielding plate is made of a material that shields the radiation R, for example, lead. The shielding plates are disposed on each side of a quadrangle, in other words, are assembled in a checkered pattern and form a quadrangular irradiation opening through which the radiation R is transmitted. The irradiation field limiter 37 changes the position of each shielding plate to change the size of the irradiation opening, thereby changing the irradiation field of the radiation R to the radiation detector 21. The radiation R having a quadrangular pyramid shape is emitted from the radiation source 20 by the operation of the irradiation field limiter 37. An irradiation angle θ of the radiation R is, for example, 45°.

Figure 7:
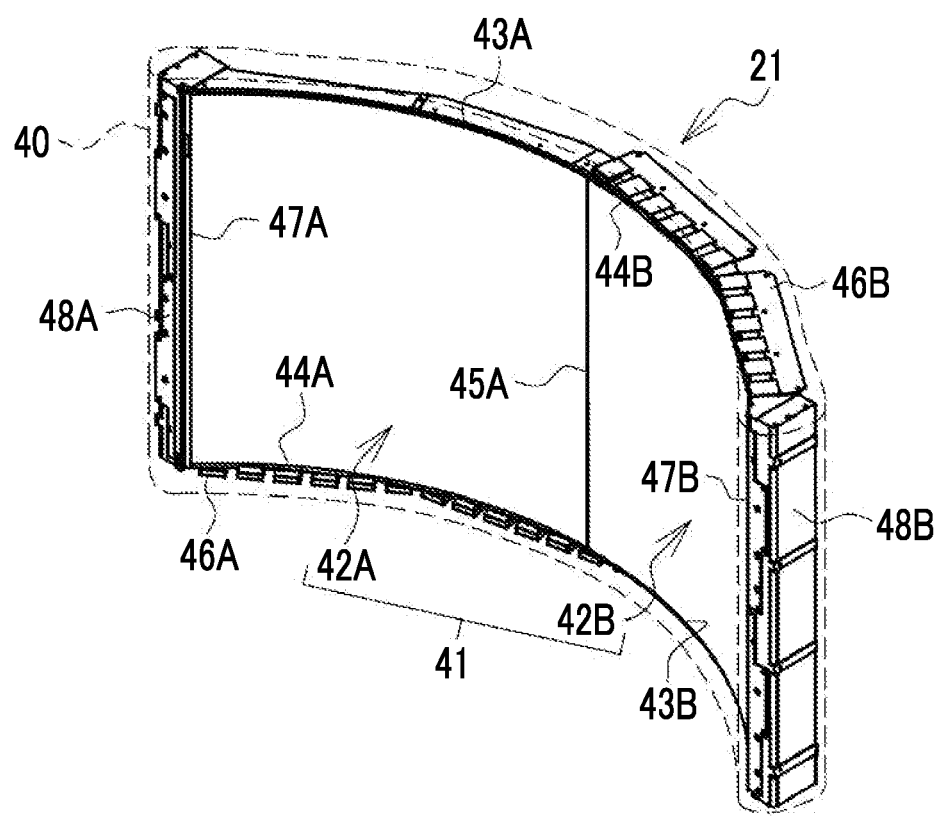
FIG. 7 is a perspective view illustrating the inside of the radiation detector.

For example, as illustrated in FIG. 7, the radiation detector 21 includes a housing 40 having an arc surface shape that follows the shape of the frame 18. The housing 40 is made of, for example, carbon. A sensor panel unit 41 is accommodated in the housing 40. The sensor panel unit 41 includes two sensor panels 42A and 42B which have a rectangular plate shape and use TFTs. The sensor panels 42A and 42B have a square shape having a size of, for example, 17 inches (about 432 mm×about 432 mm). In the sensor panel 42A, opposite sides 43A and 44A are curved in an arc shape that follows the shape of the frame 18. Similarly, in the sensor panel 42B, opposite sides 43B and 44B are curved in an arc shape that follows the shape of the frame 18. The sensor panels 42A and 42B overlap each other on sides 45A and 45B that are not curved in an arc shape (see FIG. 8 and the like for the side 45B). Further, the sensor panel 42A is an example of a "first sensor panel" according to the technology of the present disclosure, and the sensor panel 42B is an example of a "second sensor panel" according to the technology of the present disclosure. Further, the sides 43A, 43B, 44A, and 44B are examples of a "curved side" according to the technology of the present disclosure. Further, the sides 45A and 45B are an example of "sides other than the curved side to which the circuit board is connected" according to the technology of the present disclosure. Hereinafter, the sides 43A, 43B, 44A, and 44B are referred to as curved sides 43A, 43B, 44A, and 44B.

A reading circuit board 46A is attached to the curved side 44A, and a reading circuit board 46B is attached to the curved side 44B. The reading circuit boards 46A and 46B have a rectangular plate shape. Nothing is attached to the curved side 43A facing the curved side 44A and the curved side 43B facing the curved side 44B. The curved sides 44A and 44B and thus the reading circuit boards 46A and 46B are located at positions that are aligned with each other in a case in which they are rotated 180° about the center of the radiation detector 21. That is, the reading circuit boards 46A and 46B are disposed at the positions having a two-fold symmetrical relationship.

A switching circuit board 48A is attached to a side 47A facing the side 45A, and a switching circuit board 48B is attached to a side 47B facing the side 45B. The switching circuit boards 48A and 48B have a rectangular plate shape. The sides 47A and 47B and thus the switching circuit boards 48A and 48B are located at the positions that are aligned with each other in a case in which they are rotated 180° about the center of the radiation detector 21. That is, the switching circuit boards 48A and 48B are disposed at the positions having a two-fold symmetrical relationship. In addition, similarly to the columns 14A to 14C, hereinafter, the sensor panels 42A and 42B and each component attached thereto may be represented by only numbers without letters "A" and "B".

Figure 8:
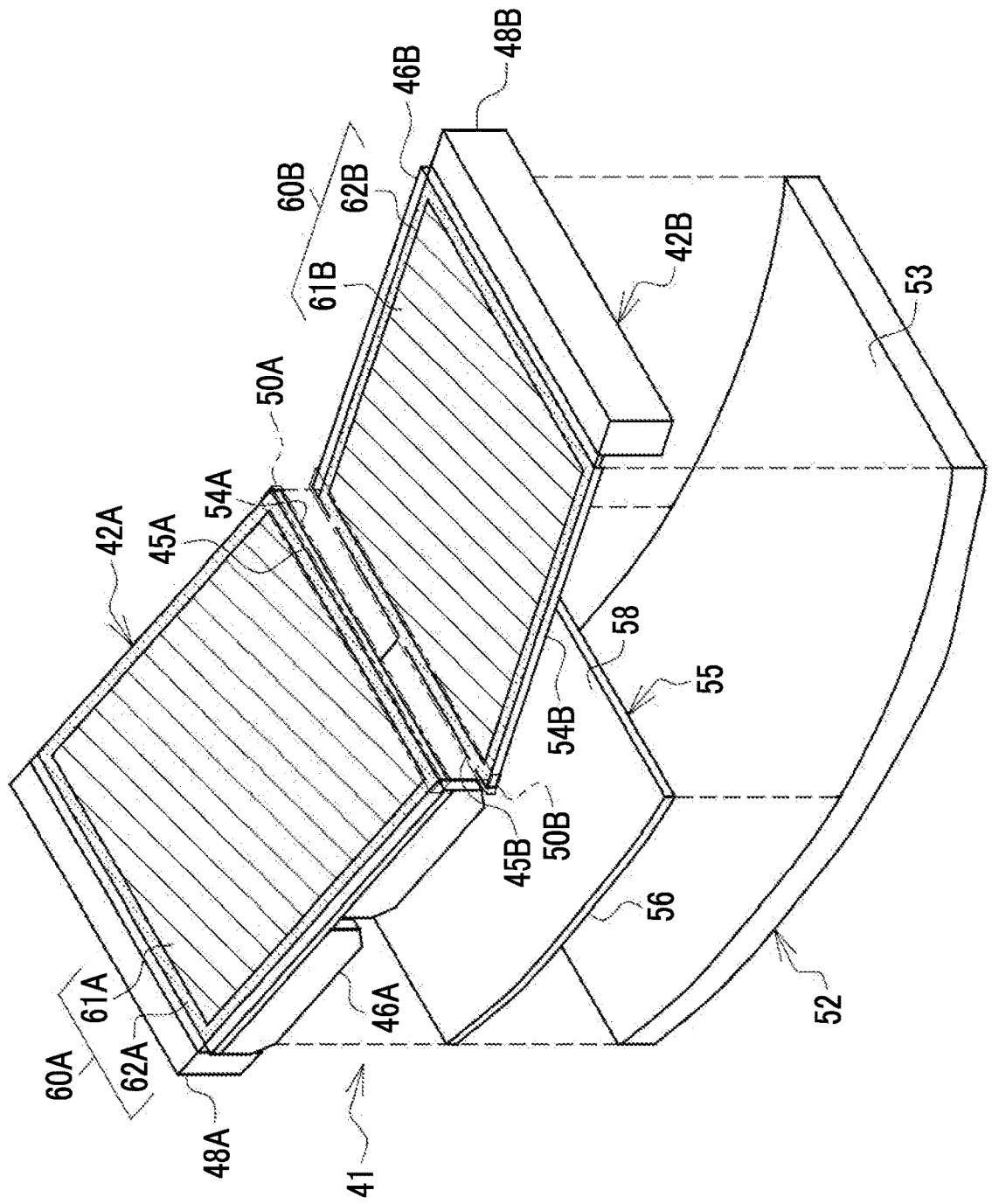
FIG. 8 is an exploded perspective view illustrating two sensor panels, a spacer, and a support table.
Figure 9:
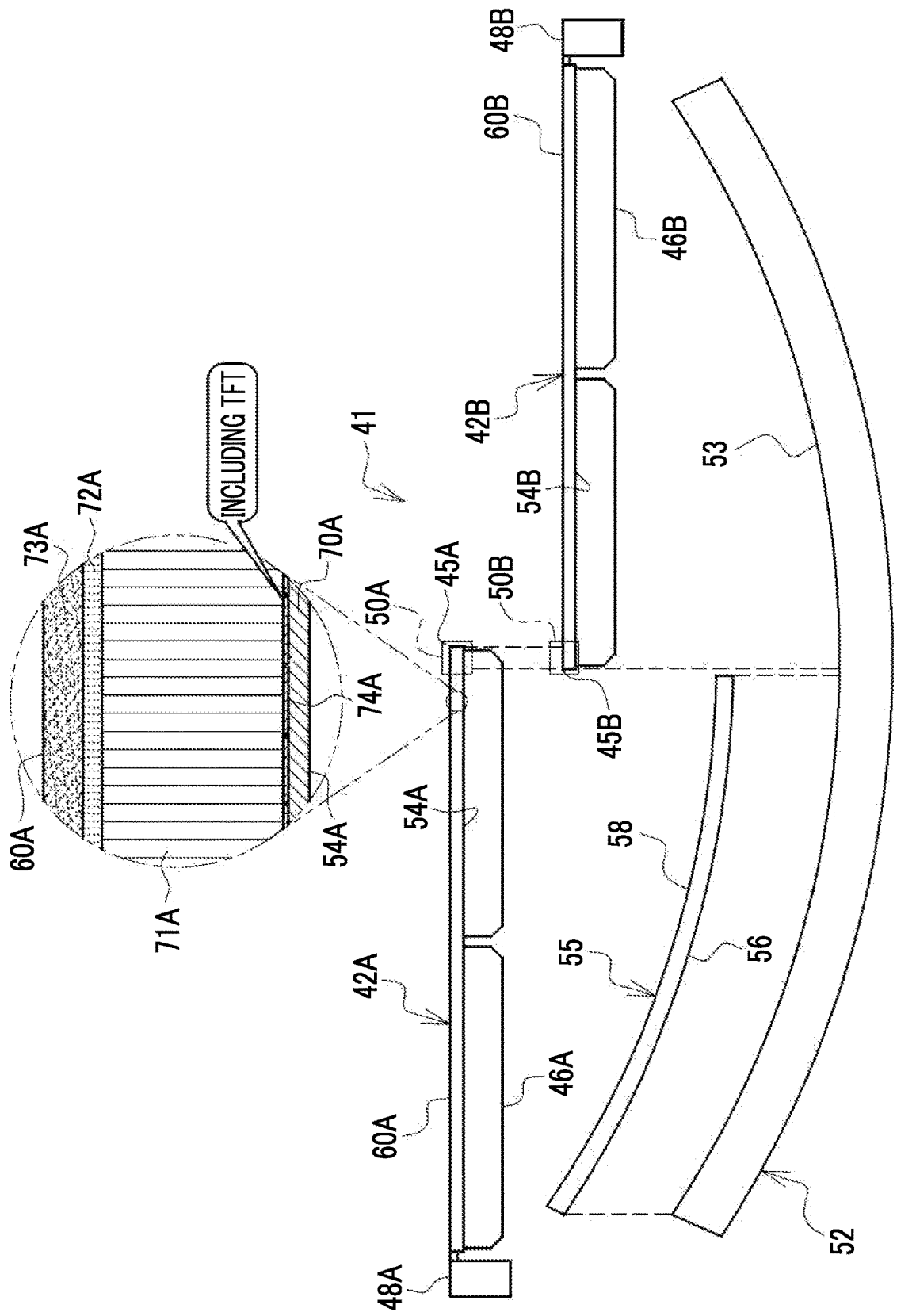
FIG. 9 is an exploded plan view illustrating the two sensor panels, the spacer, and the support table.

For example, as illustrated in FIGS. 8 and 9, in the sensor panels 42A and 42B, an end portion 50A on the side 45A and an end portion 50B on the side 45B are disposed so as to overlap each other in a thickness direction in a state in which the sides 45A and 45B are parallel to each other. The sensor panel 42A and the sensor panel 42B are fixed in the end portions 50A and 50B. The sensor panel 42A and the sensor panel 42B are fixed with, for example, a double-sided tape that is partially attached to the end portion 50B or an adhesive that is partially applied or mask-printed onto the end portion 50B. The sensor panels 42A and 42B are disposed in the order of the sensor panel 42A and the sensor panel 42B as viewed from the radiation source 20. That is, the sensor panel 42A is disposed closer to the incident side of the radiation R than the sensor panel 42B in the thickness direction.

The sensor panel unit 41 is attached to a support table 52. The support table 52 is made of metal, such as aluminum or copper, and has an attachment surface 53 that is accurately processed in an arc surface shape (U-shape) which is convex toward the opposite side of the radiation source 20 so as to follow the shape of the frame 18. The sensor panel unit 41 is attached to the attachment surface 53 in a state in which it is curved following the arc surface shape. The distortion of the radiographic image is removed by curving the sensor panel unit 41 in a curved surface shape such that the irradiation distance of the radiation R from the radiation source 20 to the entire surface of the sensor panel 42 is substantially the same. The radius of the attachment surface 53 is, for example, 500 mm. A member (not illustrated) that is made of, for example, lead and shields the radiation R is attached to a surface of the support table 52 which is opposite to the attachment surface 53. The arc surface shape is an example of a "curved surface shape" according to the technology of the present disclosure. Here, the "U-shape" is a shape in which the entire surface of the sensor panels 42A and 42B including imaging regions 61A and 61B, which will be described below, and the end portions 50A and 50B which overlap each other is curved. Specifically, the "U-shape" means a shape in which both end portions protrude toward one side and both end portions and a central portion are connected by a curved surface.

A spacer 55 is disposed between a first surface 54A of the sensor panel 42A and the attachment surface 53 of the support table 52. The spacer 55 is a thin plate that has substantially the same size as the sensor panel 42A and has an arc surface shape following the shape of the attachment surface 53. The spacer 55 has a thickness corresponding to the distance between the sensor panel 42A and the support table 52. In other words, the spacer 55 has a thickness that fills the step between the sensor panels 42A and 42B in the thickness direction caused by the overlap of the sensor panels 42A and 42B. The radius of the sensor panel 42A is, for example, 500 mm, and the radius of the sensor panel 42B is, for example, 501 mm. In this case, the step between the sensor panels 42A and 42B in the thickness direction is 1 mm, and the thickness of the spacer 55 is also 1 mm.

A first surface 56 of the spacer 55 is entirely attached to the attachment surface 53, and a second surface 58 opposite to the first surface 56 faces the first surface 54A of the sensor panel 42A. The spacer 55 and the attachment surface 53 are fixed, for example, with a double-sided tape that is attached to the attachment surface 53 or an adhesive that is applied or mask-printed onto the attachment surface 53. The first surface 54A of the sensor panel 42A and the second surface 58 of the spacer 55 are in contact with each other, but are not fixed.

A first surface 54B of the sensor panel 42B is fixed to the attachment surface 53. The sensor panel 42B and the attachment surface 53 are fixed, for example, with a double-sided tape that is partially attached to the attachment surface 53 or an adhesive that is partially applied or mask-printed onto the attachment surface 53.

A second surface 60A of the sensor panel 42A which is opposite to the first surface 54A has an imaging region 61A which has a square shape and in which pixels 74A (see FIG. 9) are arranged and a non-imaging region 62A which has a rectangular ring shape and surrounds the imaging region 61A and in which the pixels 74A are not arranged. Similarly, a second surface 60B of the sensor panel 42B which is opposite to the first surface 54B has an imaging region 61B and a non-imaging region 62B.

In FIG. 9, the sensor panel 42A has a substrate 70A and a scintillator 71A. The scintillator 71A includes, for example, terbium-activated gadolinium oxysulfide (GOS; $Gd_2O_2S:Tb$) and converts the radiation R into visible light. The scintillator 71A is attached to a support 73A through a pressure-sensitive adhesive layer 72A. The support 73A is made of, for example, white polyethylene terephthalate (PET). A rear surface of the substrate 70A is the first surface 54A, and a front surface of the support 73A is the second surface 60A.

The substrate 70A is a flexible thin film sheet that is made of a resin such as polyimide. The substrate 70A includes fine particles of an inorganic oxide that absorbs backscattered rays. Examples of the inorganic oxide include silicon dioxide ($SiO_2$), magnesium oxide (MgO), aluminum oxide (so-called alumina, $Al_2O_3$), and titanium oxide ($TIO_2$). An example of the substrate 70A having the above-mentioned features is XENOMAX (registered trademark) manufactured by Xenomax Japan Co., Ltd.

The substrate 70A is provided with the pixels 74A that detect the visible light converted from the radiation R by the scintillator 71A. As is well known, the pixel 74A includes a light receiving unit that senses the visible light and generates charge and a TFT as a switching element that reads out the charge accumulated in the light receiving unit. A plurality of signal lines for inputting the charge of the light receiving units to the reading circuit board 46A and a plurality of scanning lines for giving on/off signals (scanning signals) from the switching circuit board 48A to the TFTs are provided on the substrate 70A so as to intersect each other in the vertical and horizontal directions. The pixels 74A are disposed at the intersections of the plurality of signal lines and scanning lines. That is, the pixels 74A are two-dimensionally arranged. The pitch of the pixels 74A is, for example, 150 μm. In addition, the pixel 74A may not sense the visible light converted from the radiation R, but may directly sense the radiation R to generate charge.

Figure 10:
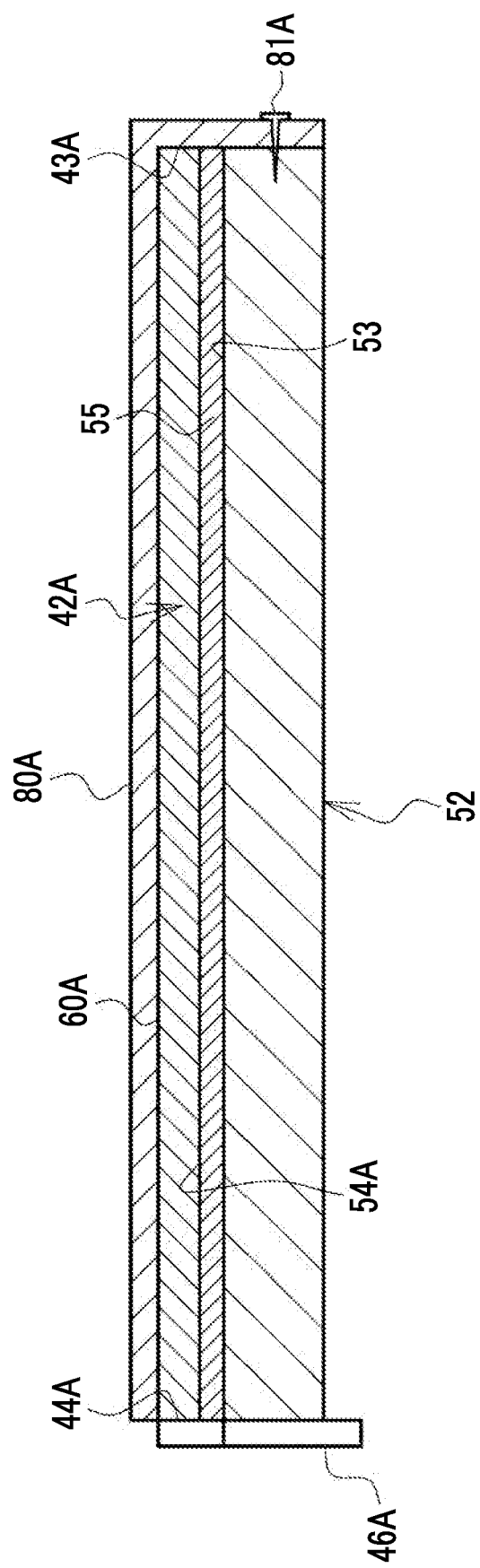
FIG. 10 is a cross-sectional view illustrating a conductive member that covers the sensor panel.

For example, as illustrated in FIG. 10, the second surface 60A of the sensor panel 42A is covered with a conductive member 80A. The conductive member 80A is a thin plate that is made of metal, such as aluminum, and shields external noise. The conductive member 80A is bent 90° on the curved side 43A facing the curved side 44A to which the reading circuit board 46A is connected, and the bent portion is fixed to the support table 52 by a plurality of pins 81A. Similarly, the second surface 60B of the sensor panel 42B is also covered with a conductive member, which is not illustrated. The conductive member covering the second surface 60B is bent 90° on the curved side 43B facing the curved side 44B to which the reading circuit board 46B is connected, and the bent portion is fixed to the support table 52 by a plurality of pins.

Since the sensor panels 42A and 42B have the same basic configuration, such as the same attachment structure of the reading circuit boards 46A and 46B, the sensor panel 42A will be mainly described below.

Figure 11:
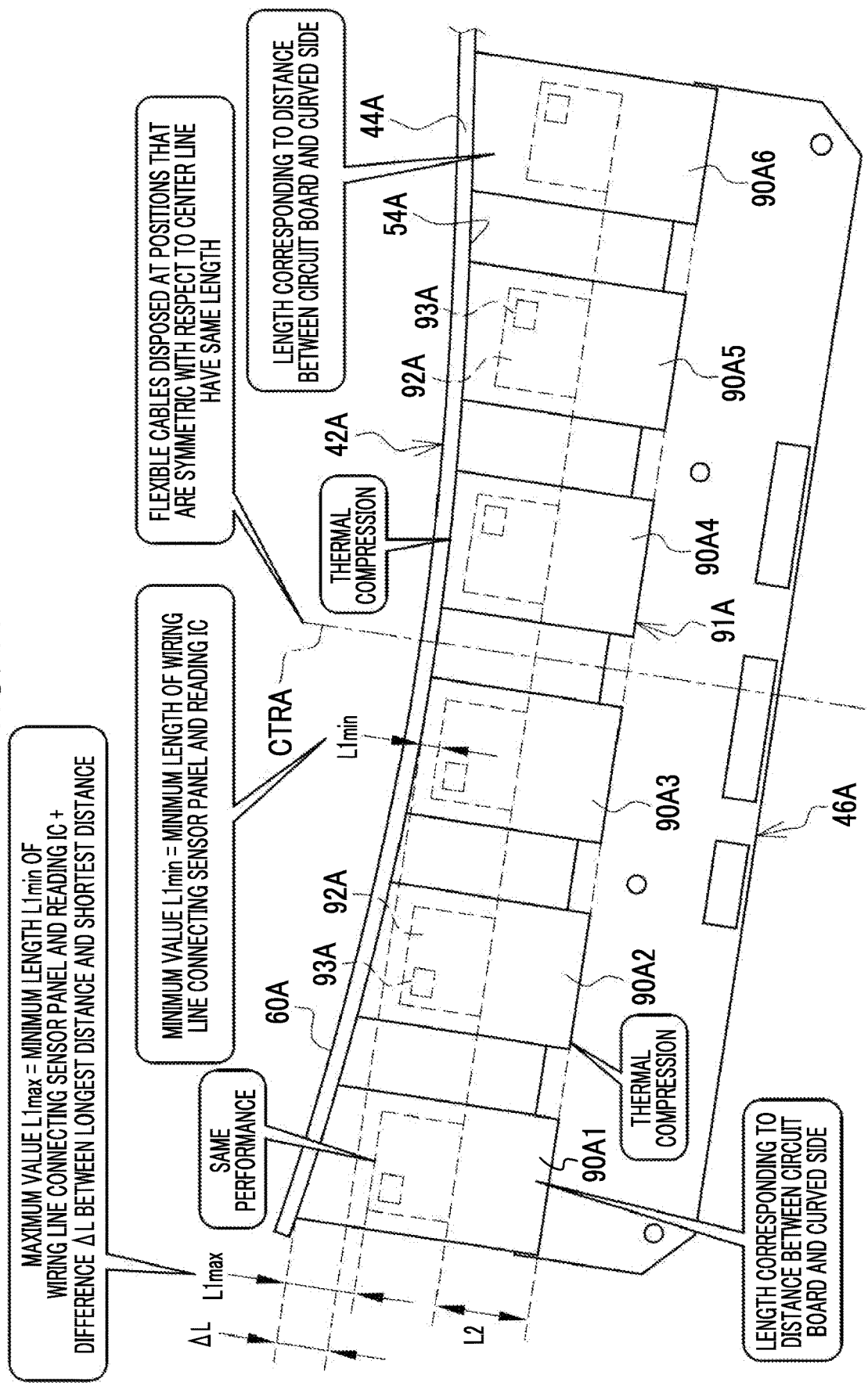
FIG. 11 is a diagram illustrating a connection structure between the sensor panel and a reading circuit board.

For example, as illustrated in FIG. 11, the reading circuit board 46A is connected to the curved side 44A of the sensor panel 42A by flexible cables 90A1, 90A2, 90A3, 90A4, 90A5, and 90A6. The flexible cables 90A1 to 90A6 are arranged at equal intervals along the curved side 44A. The flexible cables 90A1 to 90A6 have one end thermally compressed to the curved side 44A and the other end thermally compressed to the reading circuit board 46A. The thermal compression of the flexible cables 90A1 to 90A6 to the curved side 44A and the reading circuit board 46A is completed before the sensor panel 42A is attached to the attachment surface 53 of the support table 52.

In the flexible cables 90A1 to 90A6, one end on the curved side 44A is bent toward the support table 52 in order to dispose the reading circuit board 46A toward the support table 52 at an angle of 90° with respect to the sensor panel 42A. Therefore, the wiring direction of the signal lines of the sensor panel 42A is aligned with the thickness direction of the reading circuit board 46A. 90° is an example of a "set angle" according to the technology of the present disclosure. In addition, similarly to, for example, the above-mentioned "0°" and "60°", "90°" indicates, for example, "90°" including an error (for example, an error of about 1% to 10%) that is generally allowed in the technical field to which the technology of the present disclosure belongs and does not depart from the gist of the technology of the present disclosure in addition to perfect "90°".

The flexible cables 90A1 to 90A6 have a length corresponding to the distance between the reading circuit board 46A and the curved side 44A. Specifically, the flexible cables 90A3 and 90A4 disposed at the position where the distance between the reading circuit board 46A and the curved side 44A is the shortest have the shortest length. On the other hand, the flexible cables 90A1 and 90A6 disposed at the position where the distance between the reading circuit board 46A and the curved side 44A is the longest have the longest length. The flexible cables 90A2 and 92A5 disposed at the position where the distance between the reading circuit board 46A and the curved side 44A is medium have a medium length. A reduction structure 91A that reduces the bias of the stretching force applied to the flexible cables 90A1 to 90A6 caused by the curved side 44A is achieved by the flexible cables 90A1 to 90A6 having a length corresponding to the distance between the reading circuit board 46A and the curved side 44A.

The flexible cable 90A1 and the flexible cable 90A6 are disposed at positions that are symmetric with respect to a center line CTRA of the reading circuit board 46A. Similarly, the flexible cable 90A2 and the flexible cable 90A5 are disposed at positions that are symmetric with respect to the center line CTRA, and the flexible cable 90A3 and the flexible cable 90A4 are disposed at positions that are symmetric with respect to the center line CTRA. Therefore, the flexible cable 90A1 and the flexible cable 90A6 have the same length, the flexible cable 90A2 and the flexible cable 90A5 have the same length, and the flexible cable 90A3 and the flexible cable 90A4 have the same length. Further, the term "same" in the "same length" indicates "same" including an error (for example, an error of about 1% to 10%) that is generally allowed in the technical field to which the technology of the present disclosure belongs and does not depart from the gist of the technology of the present disclosure, in addition to exact "same".

A reading integrated circuit (hereinafter, abbreviated to a reading IC) 92A is mounted on each of the flexible cables 90A1 to 90A6. The reading ICs 92A have the same performance. Furthermore, similarly to the term "same" in the "same length", the term "same" in the "same performance" indicates "same" including an error that is generally allowed in the technical field to which the technology of the present disclosure belongs and does not depart from the gist of the technology of the present disclosure, in addition to exact "same".

The reading IC 92A is provided with an analog/digital converter (hereinafter, abbreviated to an A/D converter) 93A. The A/D converter 93A converts an analog signal indicated by the charge read out from the pixel 74A into a digital signal and outputs the converted digital signal to the reading circuit board 46A. Further, the reading IC 92A is provided with, for example, a correlated double sampling (CDS) circuit, in addition to the A/D converter 93A.

Lengths L1 from the sensor panel 42A to the reading ICs 92A of the flexible cables 90A1 to 90A6 including a length L1max from the sensor panel 42A to the reading IC 92A of the flexible cable 90A1 and a length L1min from the sensor panel 42A to the reading IC 92A of the flexible cable 90A3 are lengths corresponding to the distance between the reading circuit board 46A and the curved side 44A. On the other hand, lengths L2 from the reading ICs 92A of the flexible cables 90A1 to 90A6 to the reading circuit board 46A are the same.

The length L1 from the sensor panel 42A to the reading IC 92A is the minimum value L1min in the flexible cables 90A3 and 90A4 disposed at the position where the distance between the reading circuit board 46A and the curved side 44A is the shortest (in FIG. 11, the length L1min is illustrated only for the flexible cable 90A3). Further, the length L1 from the sensor panel 42A to the reading IC 92A is the maximum value L1max in the flexible cables 90A1 and 90A6 disposed at the position where the distance between the reading circuit board 46A and the curved side 44A is the longest (in FIG. 11, the length L1 max is illustrated only for the flexible cable 90A1). The length L1min is the minimum length of a wiring line connecting the sensor panel 42A and the reading IC 92A. In addition, the length L1max is a length obtained by adding a difference ΔL between the longest distance and the shortest distance among the distances between the reading circuit board 46A and the curved side 44A to the length L1min. The longest distance among the distances between the reading circuit board 46A and the curved side 44A is the length of the flexible cables 90A1 and 90A6 disposed at the position where the distance between the reading circuit board 46A and the curved side 44A is the longest. Further, the shortest distance among the distances between the reading circuit board 46A and the curved side 44A is the length of the flexible cables 90A3 and 90A4 disposed at the position where the distance between the reading circuit board 46A and the curved side 44A is the shortest.

Figure 12:
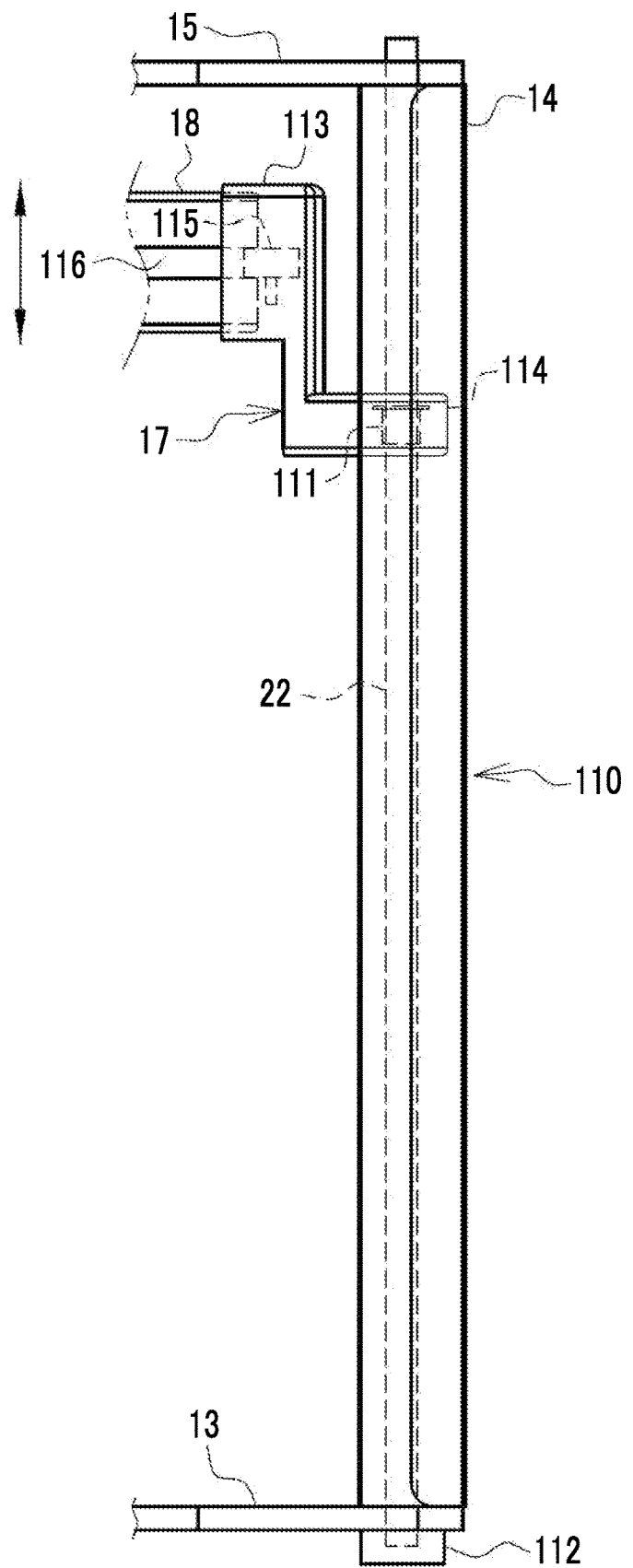
FIG. 12 is a diagram illustrating an elevating mechanism.

For example, as illustrated in FIG. 12, an elevating mechanism 110 that raises and lowers the connection member 17 and thus the frame 18 in the vertical direction is a ball screw mechanism including, for example, the screw shaft 22, a nut 111 that has a ball provided therein and is engaged with the screw shaft 22, an elevating motor 112 that rotates the screw shaft 22. The elevating motor 112 is attached to the rear surface of the stage 13. The height position of the frame 18 is determined from the rotation direction and rotation speed of the elevating motor 112.

The connection member 17 has a first connection portion 113 that is connected to the frame 18 and a second connection portion 114 that is connected to the column 14. The first connection portion 113 protrudes toward the frame 18, and the second connection portion 114 protrudes toward the column 14. The connection member 17 has a Z-shape as a whole. A bearing 115 is provided in the first connection portion 113. The bearing 115 is fitted to a guide groove 116

(see also FIG. 1 and the like) that is formed over the entire circumference of the frame 18. The bearing 115 rolls as the frame 18 is rotated. The nut 111 is provided in the second connection portion 114.

Figure 13:
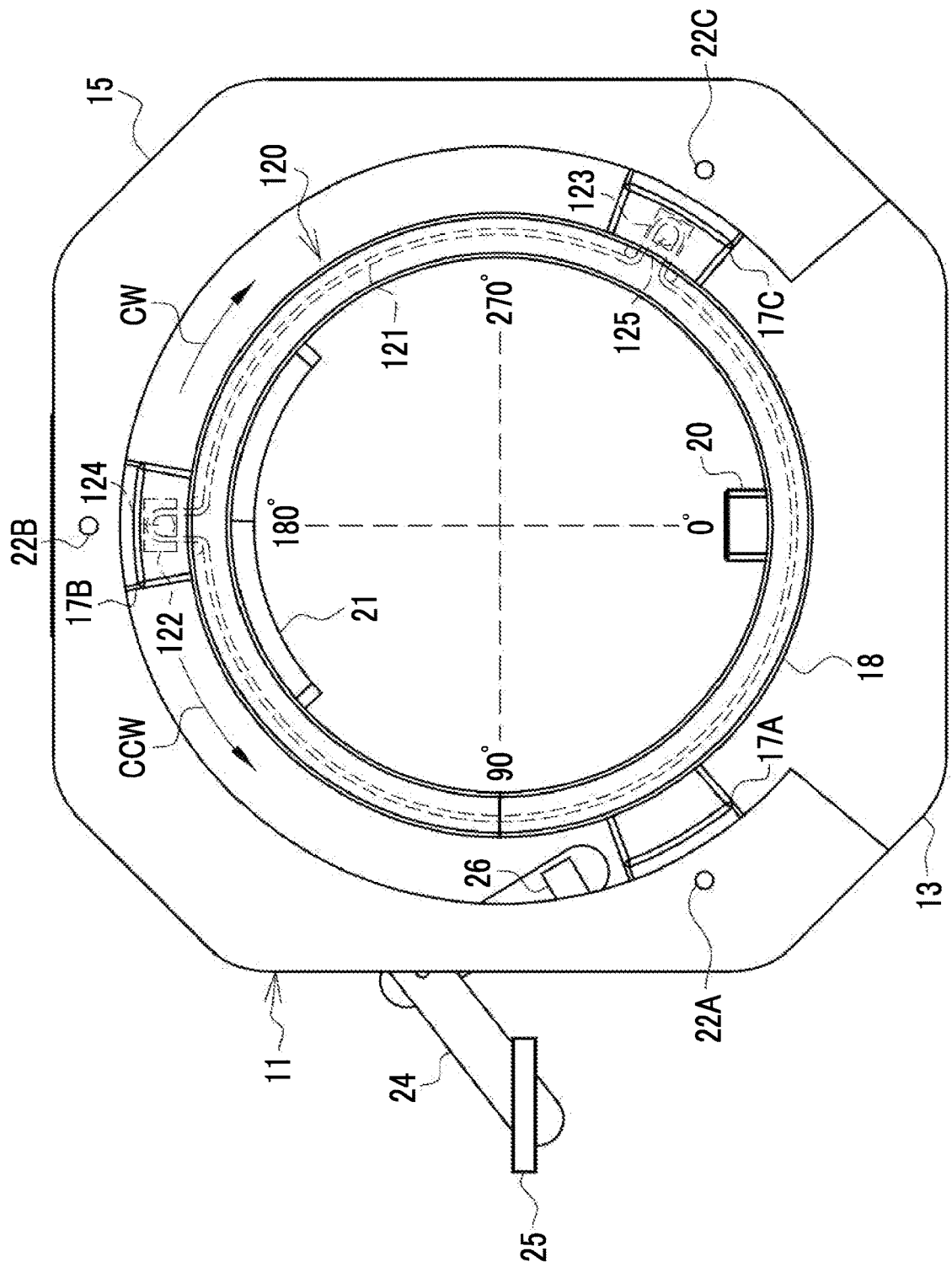
FIG. 13 is a diagram illustrating a rotation mechanism.

For example, as illustrated in FIG. 13, a rotation mechanism 120 that rotates the frame 18 around the subject S includes a rotation belt 121 that is wound around the entire circumference of the frame 18, a rotary motor 122, a potentiometer 123, and the like. The rotary motor 122 is provided in the connection member 17B and is connected to a portion of the rotation belt 121 drawn out from the frame 18 through a pulley 124. The rotary motor 122 is driven to rotate the frame 18 in a clockwise (right-hand rotation) direction CW and a counterclockwise (left-hand rotation) direction CCW. The potentiometer 123 is provided in the connection member 17C and is connected to a portion of the rotation belt 121 drawn out from the frame 18 through the pulley 125. The potentiometer 123 has a variable resistor whose resistance value is changed depending on the rotation position of the frame 18 and outputs a voltage signal corresponding to the rotation position of the frame 18. The rotation position of the frame 18 is determined by the voltage signal from the potentiometer 123.

Figure 14:
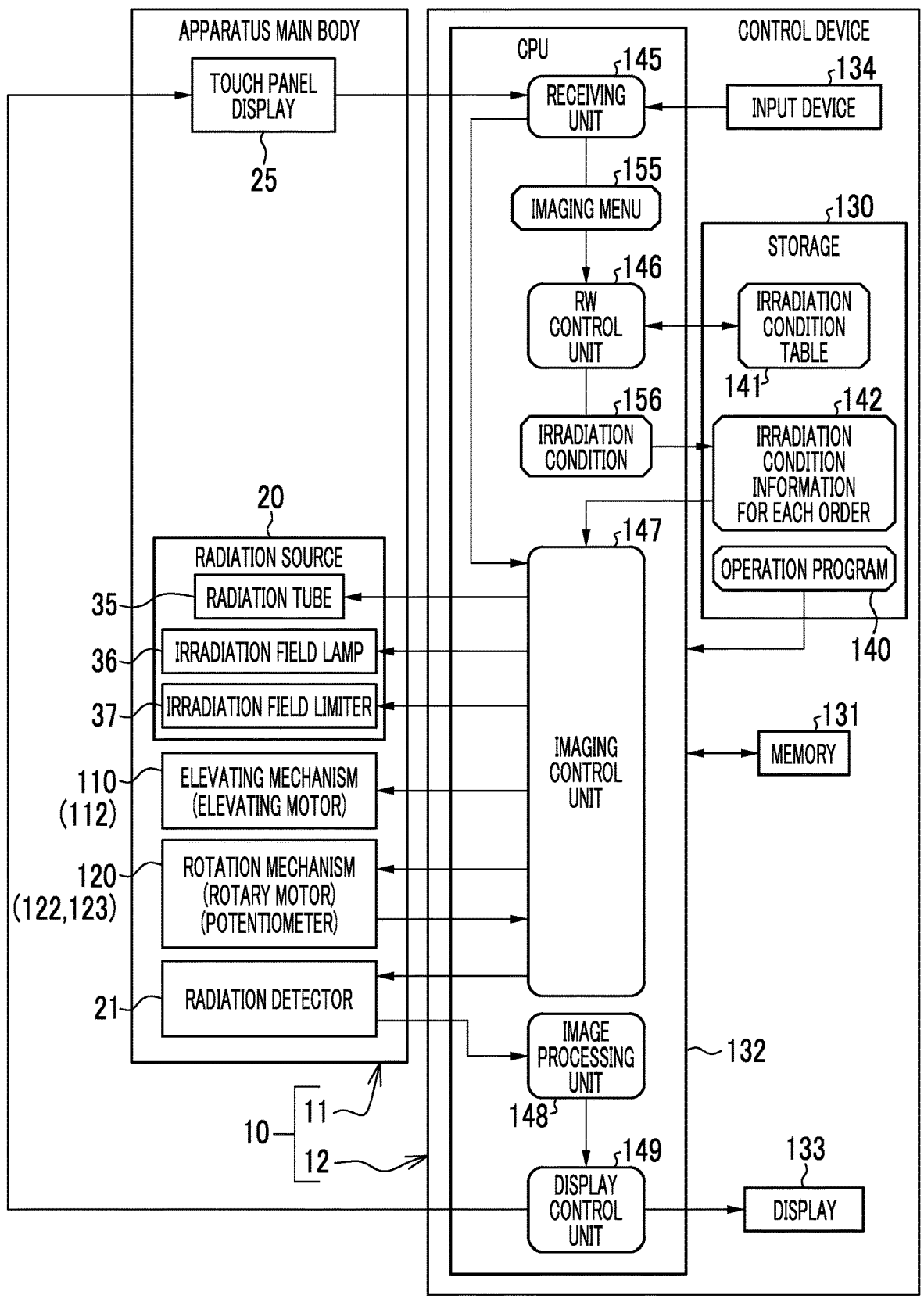
FIG. 14 is a block diagram illustrating a processing unit of a CPU of a control device.

For example, as illustrated in FIG. 14, a computer constituting the control device 12 comprises a storage 130, a memory 131, a central processing unit (CPU) 132, a display 133, an input device 134, and the like.

The storage 130 is a hard disk drive that is provided in the computer constituting the control device 12 or is connected to the computer through a cable or a network. Alternatively, the storage 130 is a disk array in which a plurality of hard disk drives are connected. The storage 130 stores, for example, a control program, such as an operating system, various application programs, and various kinds of data associated with these programs. In addition, a solid state drive may be used instead of the hard disk drive.

The memory 131 is a work memory that is used by the CPU 132 to perform processes. The CPU 132 loads the program stored in the storage 130 to the memory 131 and performs the process corresponding to the program. Therefore, the CPU 132 controls the overall operation of each unit of the computer. In addition, the memory 131 may be provided in the CPU 132.

The display 133 displays various screens. The various screens have operation functions by a graphical user interface (GUI). The computer constituting the control device 12 receives operation instructions input from the input device 134 through various screens. The input device 134 is, for example, a keyboard, a mouse, a touch panel, and a microphone for voice input.

An operation program 140 is stored in the storage 130. The operation program 140 is an application program for causing the computer to function as the control device 12. The storage 130 stores, for example, an irradiation condition table 141 and irradiation condition information 142 for each order, in addition to the operation program 140.

In a case in which the operation program 140 is started, the CPU 132 of the control device 12 functions as a receiving unit 145, a read and write (hereinafter, abbreviated to RW) control unit 146, an imaging control unit 147, an image processing unit 148, and a display control unit 149 in cooperation with, for example, the memory 131.

The receiving unit 145 receives various operation instructions input by the operator through the touch panel display 25 of the apparatus main body 11 and the input device 134. For example, the receiving unit 145 receives an imaging menu 155. The receiving unit 145 outputs the imaging menu 155 to the RW control unit 146.

The RW control unit 146 receives the imaging menu 155 from the receiving unit 145. The RW control unit 146 reads out irradiation conditions 156 of the radiation R which correspond to the received imaging menu 155 from the irradiation condition table 141. The RW control unit 146 writes the irradiation conditions 156 read from the irradiation condition table 141 to the irradiation condition information 142 for each order.

The imaging control unit 147 controls the operation of the radiation source 20 (the radiation tube 35, the irradiation field lamp 36, and the irradiation field limiter 37), the elevating mechanism 110 (elevating motor 112), the rotation mechanism 120 (the rotary motor 122 and the potentiometer 123), and the radiation detector 21. The imaging control unit 147 reads out the irradiation conditions 156 from the irradiation condition information 142 for each order. The imaging control unit 147 drives the irradiation field limiter 37 according to the irradiation conditions 156 to adjust the irradiation field. Further, the imaging control unit 147 drives the radiation tube 35 according to the irradiation conditions 156 such that the radiation R is emitted from the radiation tube 35. The imaging control unit 147 outputs a radiographic image, which has been formed by the emission of the radiation R and detected by the radiation detector 21, from the radiation detector 21 to the image processing unit 148. Hereinafter, the radiographic image detected by the radiation detector 21 is referred to as a projection image.

The image processing unit 148 acquires the projection image from the radiation detector 21. The image processing unit 148 performs various types of image processing on the projection image. Further, the image processing unit 148 performs a reconstruction process on a plurality of projection images subjected to the image processing to generate a tomographic image TI. The image processing unit 148 outputs the projection image or the tomographic image TI subjected to the image processing to the display control unit 149. In addition, the image processing unit 148 may perform a process of correcting the positional deviation of the pixels 74 caused by the thermal expansion and contraction of the sensor panel 42.

The display control unit 149 controls the display of various kinds of information on the touch panel display 25 and the display 133. The display control unit 149 receives the projection image or the tomographic image TI from the image processing unit 148. The display control unit 149 displays the projection image or the tomographic image TI on the touch panel display 25 and the display 133.

The imaging menu 155 includes, for example, imaging order identification data (ID) and an imaging procedure (see FIG. 15). The imaging order ID is identification information of the imaging order issued by a doctor who performs a medical examination using the tomographic image TI. The imaging procedure includes the posture of the subject S in a standing or sitting position, an imaging part, such as the head, the neck, or the spine, and the attributes of the subject S such as an adult male and an adult female.

The imaging order is transmitted from a radiology information system (RIS) (not illustrated) to the control device 12. The control device 12 displays a list of imaging orders on the display 133 under the control of the display control unit 149. The operator browses the list of imaging orders and checks the content of the list. Then, the control device 12 displays the imaging menu 155 corresponding to the imaging order on the display 133 such that it can be set. The operator operates the input device 134 to select the imaging menu 155 corresponding to the imaging order and to input the imaging menu 155.

For example, as illustrated in FIG. 15, the irradiation conditions 156 are registered in the irradiation condition table 141 for each imaging procedure. The irradiation conditions 156 include a tube voltage and a tube current applied to the radiation tube 35 and the irradiation time of the radiation R. In addition, the irradiation conditions 156 include the size of the irradiation field, which is not illustrated. The operator can finely adjust the irradiation conditions 156 by hand. Further, instead of the tube current and the irradiation time, a tube current-irradiation time product, that is, a so-called mAs value may be set as the irradiation condition 156.

A scout imaging position and a main imaging start position are also registered in the irradiation condition table 141 for each imaging procedure, which is not illustrated. The scout imaging position is a set of the height position and the rotation position of the frame 18 in scout imaging. The height position indicates the height of the frame 18 in a case in which the surface of the stage 13 is 0 cm. The rotation position is, for example, a position where the radiation source 20 faces the subject S, that is, a position of 0°. Alternatively, the rotation position may be a position of 90° where the radiation source 20 faces the right side surface of the subject S or a position of 270° where the radiation source 20 faces the left side surface of the subject S.

Here, the scout imaging is preliminary radiography that is performed to confirm the positioning of the subject S before the main imaging that captures a plurality of projection images at a predetermined angle to generate the tomographic image TI. In the scout imaging, the frame 18 is located at the height position and the rotation position registered in the irradiation condition table 141, and the radiation R is emitted with a lower dose than that in the main imaging to obtain one projection image. Hereinafter, the projection image obtained by the scout imaging is referred to as a scout image SI (see FIG. 16).

The main imaging start position is the rotation start position of the frame 18 in the main imaging. The main imaging start position is, for example, a position of 0°. Alternatively, the main imaging start position may be a position of 90°.

The irradiation conditions 156, the scout imaging position, and the main imaging start position are registered for each imaging order ID in the irradiation condition information 142 for each order, which is not illustrated. The imaging control unit 147 reads out the irradiation conditions 156, the scout imaging position, and the main imaging start position corresponding to the imaging order ID of the next imaging from the irradiation condition information 142 for each order and controls the operation of each unit on the basis of the read-out irradiation condition 156, scout imaging position, and main imaging start position.

In a case in which the subject S is guided into the apparatus main body 11, the frame 18 is moved to a retracted height position by the elevating mechanism 110 and is rotated to a position of 60° by the rotation mechanism 120 under the control of the imaging control unit 147. The retracted height position is set on the upper end side of the column 14. Specifically, the retracted height position is the position of the highest point in the elevation range of the frame 18. In this example, the position of the highest point in the elevation range of the frame 18 is the position of substantially the upper end of the column 14 and is the position where the second connection portion 114 of the connection member 17 comes into contact with the rear surface of the top plate 15. The position of 60° is a position where the entire radiation source 20 overlaps the column 14A. The operator guides the subject S into the apparatus main body 11 in this state through a space between the columns 14A and 14C as an entrance and positions the subject S.

After positioning the subject S in the apparatus main body 11, the operator stays at the installation position of the apparatus main body 11 and operates the touch panel display 25 to move the frame 18 to the height position registered in the irradiation condition table 141 and to rotate the frame 18 to the position of 0°. Then, the operator operates the touch panel display 25 to turn on the irradiation field lamp 36 and to irradiate the irradiation field with visible light, in order to confirm the irradiation field of the radiation R.

The operator visually recognizes the visible light from the irradiation field lamp 36 and determines whether the height position of the frame 18 and the positioning of the subject S are appropriate for imaging. In a case in which it is determined that the height position of the frame 18 and the positioning of the subject S are not appropriate for imaging, the operator operates the touch panel display 25 to adjust the height position of the frame 18 or to reposition the subject S. In a case in which it is determined that the height position of the frame 18 and the positioning of the subject S are appropriate for imaging, the operator operates the touch panel display 25 to turn off the irradiation field lamp 36.

Figure 16:
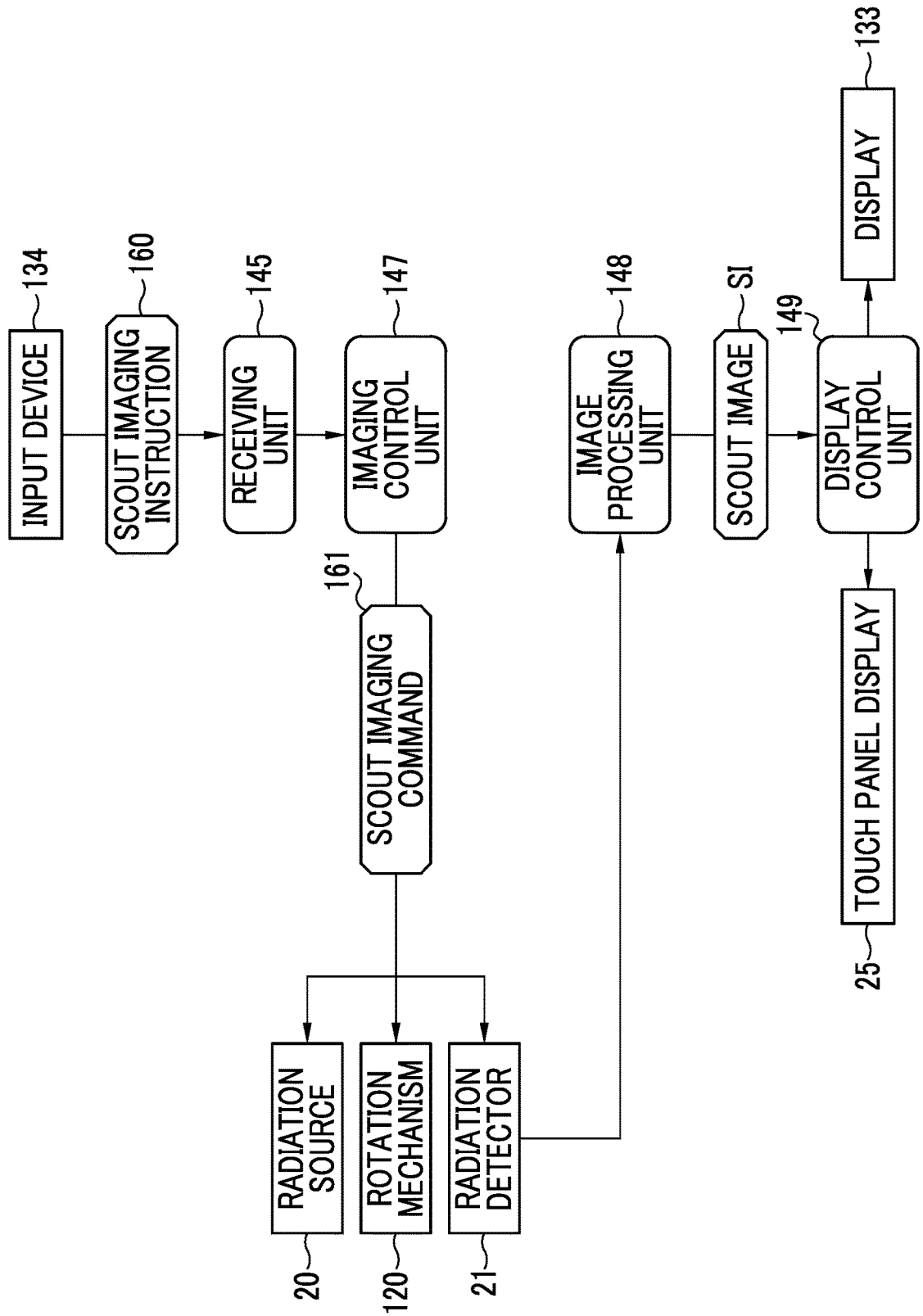
FIG. 16 is a diagram illustrating an outline of a process in a case in which a scout imaging instruction for performing scout imaging is input.

For example, as illustrated in FIG. 16, after confirming the irradiation field of the radiation R, the operator moves to the installation position of the control device 12 and operates the input device 134 to input a scout imaging instruction 160 for performing the scout imaging. The receiving unit 145 receives the scout imaging instruction 160 and outputs the instruction to the imaging control unit 147. The imaging control unit 147 outputs a scout imaging command 161 corresponding to the scout imaging instruction 160 to the radiation source 20, the radiation detector 21, and the rotation mechanism 120.

The content of the scout imaging command 161 is that the height position at the time of confirming the irradiation field of the radiation R is maintained and the frame 18 is rotated to the rotation position which is the scout imaging position registered in the irradiation condition table 141. Further, the content of the scout imaging command 161 is that the scout imaging is performed at the height position at the time of confirming the irradiation field of the radiation R and the rotation position which is the scout imaging position registered in the irradiation condition table 141. The rotation mechanism 120 drives the rotary motor 122 to rotate the rotation belt 121, thereby rotating the frame 18 to the rotation position which is the scout imaging position registered in the irradiation condition table 141.

The radiation source 20 drives the radiation tube 35 to irradiate the subject S with the radiation R for scout imaging. The radiation detector 21 detects the radiation R transmitted through the subject S to obtain the projection image. The radiation detector 21 outputs the projection image to the image processing unit 148.

The image processing unit 148 performs various types of image processing on the projection image from the radiation detector 21 to obtain the scout image SI. The image processing unit 148 outputs the scout image SI to the display control unit 149. The display control unit 149 displays the scout image SI on the touch panel display 25 and the display 133.

The operator browses the scout image SI on the display 133 and determines whether the height position of the frame 18 and the positioning of the subject S are appropriate for imaging. In a case in which it is determined that the height position of the frame 18 and the positioning of the subject S are not appropriate for imaging from the scout image SI, the operator returns to the installation position of the apparatus main body 11 and turns on the irradiation field lamp 36 again to adjust the height position of the frame 18 or to reposition the subject S.

Figure 17:
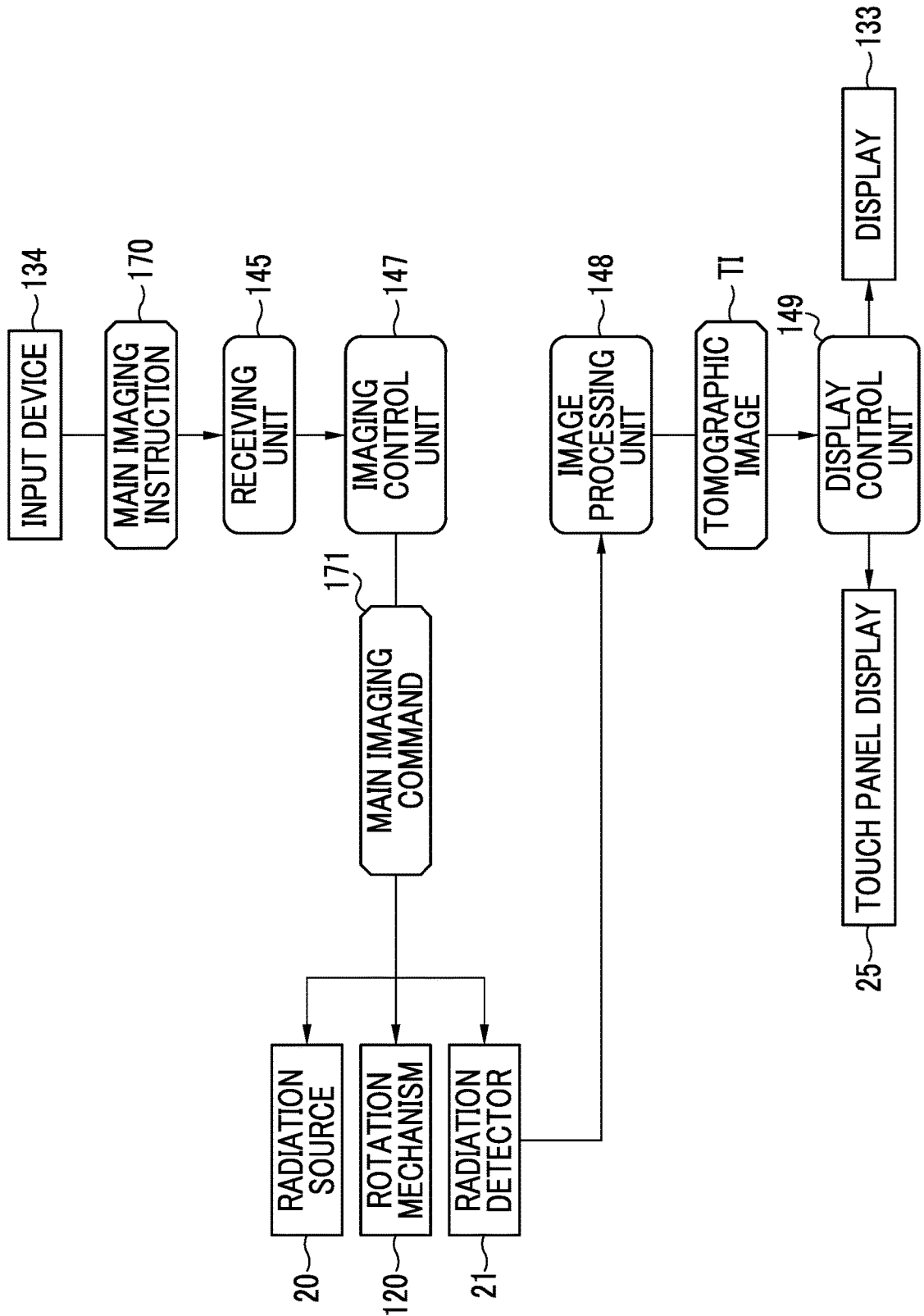
FIG. 17 is a diagram illustrating an outline of a process in a case in which a main imaging instruction for performing main imaging is input.

For example, as illustrated in FIG. 17, in a case in which it is determined that the height position of the frame 18 and the positioning of the subject S are appropriate for imaging from the scout image SI, the operator operates the input device 134 to input a main imaging instruction 170 for performing the main imaging. The receiving unit 145 receives the main imaging instruction 170 and outputs the instruction to the imaging control unit 147. The imaging control unit 147 outputs a main imaging command 171 corresponding to the main imaging instruction 170 to the radiation source 20, the radiation detector 21, and the rotation mechanism 120.

The content of the main imaging command 171 is that the height position at the time of the end of the scout imaging is maintained and the frame 18 is rotated to the main imaging start position and is then rotated to a main imaging end position in the counterclockwise direction CCW. Further, the content of the main imaging command 171 is that the main imaging is performed while the frame 18 is rotated from the main imaging start position to the main imaging end position. The rotation mechanism 120 drives the rotary motor 122 to rotate the rotation belt 121 such that the frame 18 is first rotated to the main imaging start position. Then, the rotation mechanism 120 rotates the frame 18 to the main imaging end position in the counterclockwise direction CCW. In this example, the main imaging end position is a position that is rotated by 225° in the counterclockwise direction CCW from the main imaging start position. In a case in which the main imaging start position is a position of 0°, the main imaging end position is a position of 135° that is rotated by 225° in the counterclockwise direction CCW from the position of 0°. Further, in a case in which the main imaging start position is 90°, the main imaging end position is a position of 225°. In a case in which the main imaging start position is 180°, the main imaging end position is a position of 315°.

The radiation source 20 drives the radiation tube 35 at a predetermined angle to irradiate the subject S with the radiation R for main imaging according to the irradiation conditions 156 at a predetermined angle. The radiation detector 21 detects the radiation R transmitted through the subject S at a predetermined angle to obtain a plurality of projection images. The radiation detector 21 sequentially outputs the plurality of projection images to the image processing unit 148.

The image processing unit 148 performs a reconstruction process on the plurality of projection images from the radiation detector 21 to obtain the tomographic image TI. The image processing unit 148 outputs the tomographic image TI to the display control unit 149. The display control unit 149 displays the tomographic image TI on the touch panel display 25 and the display 133.

The operator browses the tomographic image TI on the display 133 and determines whether or not the tomographic image TI needs to be re-captured. In a case in which it is determined that the tomographic image TI needs to be re-captured, the operator operates the input device 134 to re-input the main imaging instruction 170.

In a case in which it is determined that the tomographic image TI does not need to be re-captured, the operator operates the input device 134 to return the frame 18 to the retracted height position. Further, the frame 18 is rotated in the clockwise direction CW from the imaging end position and is returned to the position of 60°. Then, the operator retracts the subject S from the inside of the apparatus main body 11.

Figure 18:
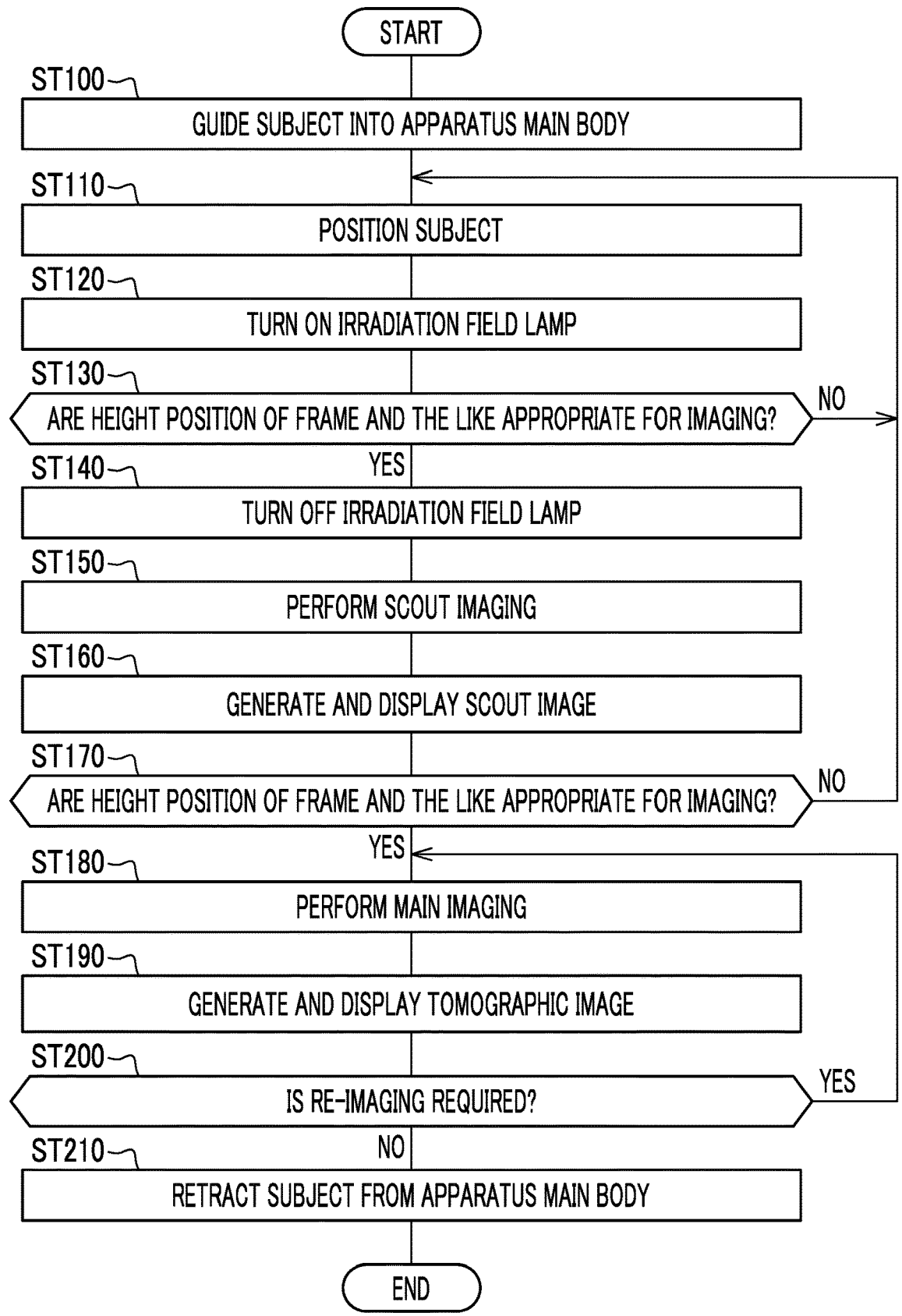
FIG. 18 is a flowchart illustrating a procedure of capturing a tomographic image by the CT apparatus.

Next, the operation of the above-mentioned configuration will be described with reference to a flowchart illustrated in FIG. 18. In a case in which the operation program 140 is started, the CPU 132 of the control device 12 functions as the receiving unit 145, the RW control unit 146, the imaging control unit 147, the image processing unit 148, and the display control unit 149 as illustrated in FIG. 14.

First, in a state in which the frame 18 is moved to the retracted height position and is rotated to the position of 60°, the operator guides the subject S into the apparatus main body 11 (Step ST100). Then, the operator positions the subject S (Step ST110).

After positioning the subject S, the operator inputs an instruction to turn on the irradiation field lamp 36 through the touch panel display 25. Then, the elevating mechanism 110 is operated to move the frame 18 to the height position registered in the irradiation condition table 141. Further, the rotation mechanism 120 is operated to rotate the frame 18 to the position of 0°. Further, after the irradiation field limiter 37 is driven and adjusted to the irradiation field corresponding to the irradiation conditions 156, the irradiation field lamp 36 is turned on, and the irradiation field is irradiated with visible light (Step ST120).

The operator determines whether or not the height position of the frame 18 and the positioning of the subject S are appropriate for imaging with reference to the visible light from the irradiation field lamp 36 (Step ST130). In a case in which the height position of the frame 18 and the positioning of the subject S are not appropriate for imaging (NO in Step ST130), the operator adjusts the height position of the frame 18 or repositions the subject S. In a case in which the height position of the frame 18 and the positioning of the subject S are appropriate for imaging (YES in Step ST130), the operator inputs an instruction to turn off the irradiation field lamp 36 through the touch panel display 25, and the irradiation field lamp 36 is turned off (Step ST140).

As illustrated in FIG. 16, after confirming the irradiation field of the radiation R, the operator inputs the scout imaging instruction 160 through the input device 134. The receiving unit 145 receives the scout imaging instruction 160. Then, the scout imaging command 161 is output from the imaging control unit 147 to, for example, the radiation source 20.

The rotation mechanism 120 is operated by the scout imaging command 161 to rotate the frame 18 to the rotation position registered in the irradiation condition table 141. Further, the radiation tube 35 irradiates the subject S with the radiation R for scout imaging, and the radiation detector 21 detects the radiation R transmitted through the subject S to obtain the projection image (Step ST150).

The image processing unit 148 performs various types of image processing on the projection image obtained by the radiation detector 21 to obtain the scout image SI. The scout image SI is displayed on the touch panel display 25 and the display 133 under the control of the display control unit 149 (Step ST160).

The operator determines whether or not the height position of the frame 18 and the positioning of the subject S are appropriate for imaging again with reference to the scout image SI (Step ST170). In a case in which the height position of the frame 18 and the positioning of the subject S are not appropriate for imaging (NO in Step ST170), the operator adjusts the height position of the frame 18 or repositions the subject S.

In a case in which the height position of the frame 18 and the positioning of the subject S are appropriate for imaging (YES in Step ST170), the operator inputs the main imaging instruction 170 through the input device 134 as illustrated in FIG. 17. The receiving unit 145 receives the main imaging instruction 170. Then, the main imaging command 171 is output from the imaging control unit 147 to, for example, the radiation source 20.

The rotation mechanism 120 is operated in response to the main imaging command 171 to first rotate the frame 18 to the main imaging start position. Then, the frame 18 is rotated to the main imaging end position in the counterclockwise direction CCW. During that time, the radiation tube 35 irradiates the subject S with the radiation R for main imaging at a predetermined angle, and the radiation detector 21 detects the radiation R transmitted through the subject S whenever the subject S is irradiated to obtain a plurality of projection images (Step ST180).

The image processing unit 148 performs the reconstruction process on the plurality of projection images obtained by the radiation detector 21 to obtain the tomographic image TI. The tomographic image TI is displayed on the touch panel display 25 and the display 133 under the control of the display control unit 149 (Step ST190).

The operator determines whether or not the tomographic image TI needs to be re-captured (Step ST200). In a case in which the operator determines that the tomographic image TI needs to be re-captured (YES in Step ST200), the operator inputs the main imaging instruction 170 through the input device 134, and the process returns to Step ST180.

In a case in which the operator determines that the tomographic image TI does not need to be re-captured (NO in Step ST200), the elevating mechanism 110 is operated in response to an instruction from the operator through the input device 134 to return the frame 18 to the retracted height position. Further, the rotation mechanism 120 is operated to return the frame 18 from the imaging end position to the position of 60° in the clockwise direction CW. After the frame 18 is returned to the retracted height position and the position of 60°, the operator retracts the subject S from the apparatus main body 11 (Step ST210). The series of Steps ST100 to ST210 is repeated in a case in which there is the next imaging order.

As described above, the radiation detector 21 comprises the support table 52 in which the attachment surface 53 having an arc surface shape is formed, the sensor panel 42 which has a rectangular plate shape and in which the pixels 74 that include TFTs and detect the radiation R are two-dimensionally arranged, the circuit board 46, the flexible cables 90, and the reduction structure 91. The sensor panel 42 is attached to the attachment surface 53 while being curved following the arc surface shape. The flexible cables 90 connect the curved side 44 of the sensor panel 42 and the reading circuit board 46 and are arranged along the curved side 44. The flexible cables 90 are bent in order to dispose the reading circuit board 46 at an angle of 90° with respect to the sensor panel 42. The reduction structure 91 reduces the bias of the stretching force applied to the flexible cables 90 caused by the curved side 44. Therefore, the concern that an excessive stretching force will be applied to the flexible cable 90 depending on the location is reduced. As a result, it is possible to reduce the concern that defects, such as cracks and malfunctions, will occur in the reading circuit board 46.

Since the reading circuit board 46 is disposed at an angle of 90° with respect to the sensor panel 42, the reading circuit board 46 does not protrude from the curved side 44 in the direction parallel to the sides 45 and 47. Therefore, it is possible to reduce the size of the radiation detector 21.

Figure 19:
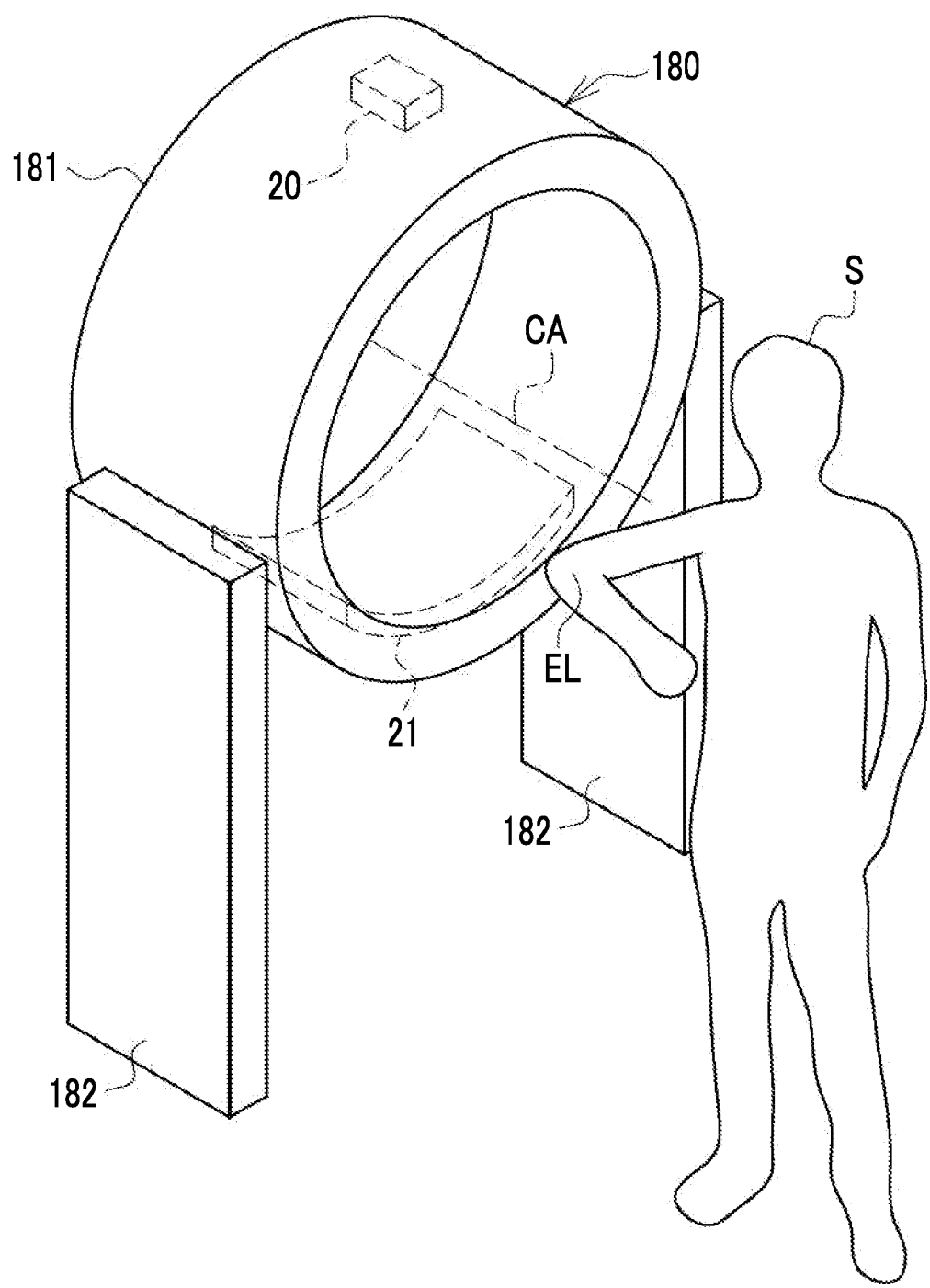
FIG. 19 is a diagram illustrating the effect of a configuration in which the reading circuit board does not protrude from a curved side.

Further, for example, in a case in which the radiation detector 21 according to this example is provided in a radiography apparatus 180 illustrated in FIG. 19, there are the following advantages. The radiography apparatus 180 comprises an annular frame 181 provided with the radiation source 20 and the radiation detector 21 and two columns 182. The columns 182 support the frame 181 such that a central axis CA of the frame 181 is orthogonal to the vertical direction.

For example, a case is considered in which an elbow EL of the subject S is inserted into the frame 181 and is imaged in the radiography apparatus 180. In a case in which the reading circuit board 46 protrudes from the curved side 44 in a direction parallel to the sides 45 and 47, the elbow EL needs to be inserted into the back of the frame 181 by the amount of protrusion of the reading circuit board 46, which imposes a burden on the subject S. However, in the radiation detector 21 according to this example, since the reading circuit board 46 does not protrude from the curved side 44 in the direction parallel to the sides 45 and 47, the amount of insertion of the elbow EL into the frame 181 is small, which makes it possible to reduce the burden on the subject S.

The reading circuit board 46 has a rectangular plate shape. The reduction structure 91 includes the flexible cables 90 having a length corresponding to the distance between the reading circuit board 46 and the curved side 44. A very simple configuration in which the length of the flexible cables 90 changes depending on the distance between the reading circuit board 46 and the curved side 44 makes it possible to reduce the bias of the stretching force applied to the flexible cables 90.

The flexible cable 90 has one end thermally compressed to the curved side 44 before being curved and the other end thermally compressed to the reading circuit board 46. The curved side 44 has a straight shape before being curved, and the reading circuit board 46 has a rectangular plate shape and straight sides as described above. Therefore, the flexible cable 90 is more easily thermally compressed to the straight side than to the curved side.

Figure 20:
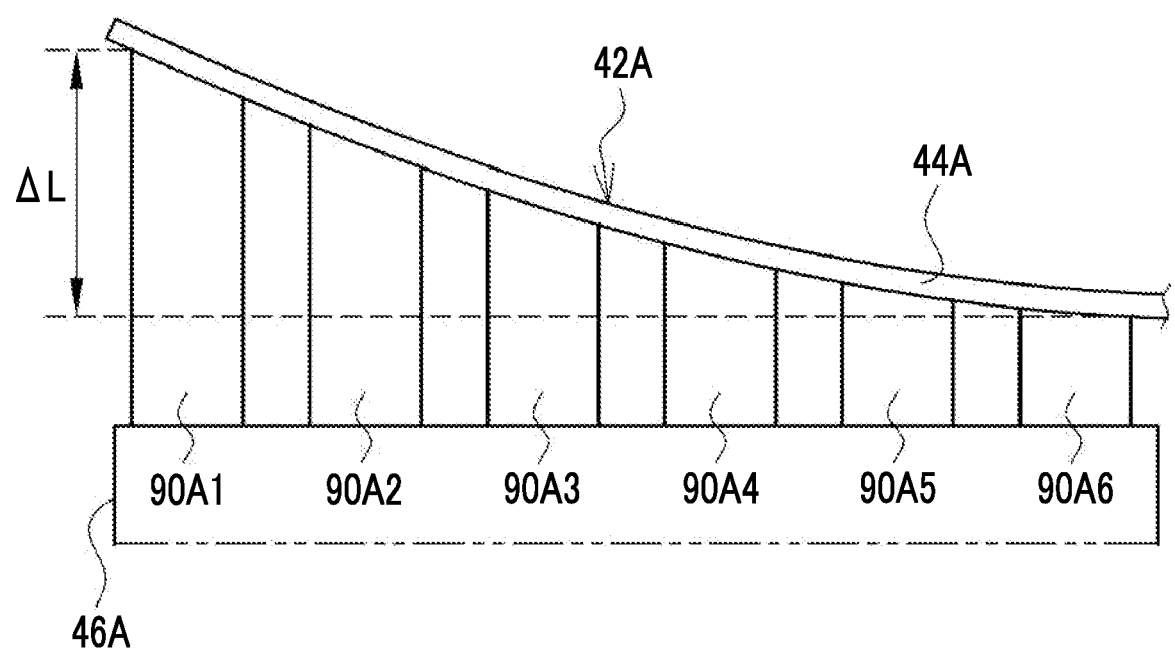
FIG. 20 is a diagram illustrating the effect of a configuration in which flexible cables disposed at positions that are symmetric with respect to a center line of the reading circuit board have the same length.

The flexible cables 90 disposed at the positions that are symmetric with respect to the center line CTR of the reading circuit board 46 have the same length. Therefore, for example, as illustrated in FIG. 20, a variation in the length of the flexible cable 90 can be less than that in a case in which the length of the flexible cable 90 changes stepwise. Further, it is possible to reduce the difference ΔL between the longest distance and the shortest distance among the distances between the reading circuit board 46 and the curved side 44. The small difference ΔL means that the lengths of the plurality of flexible cables 90 do not change so much. Therefore, the fact that the lengths of the plurality of flexible cables 90 do not change so much means that the signal transmission characteristics of the plurality of flexible cables 90 do not change so much. Therefore, it is possible to minimize the difference between the transmission characteristics of the plurality of flexible cables 90.

The reading IC 92 is mounted on the flexible cable 90. Therefore, the flexible cable 90 can perform a process such as A/D conversion.

In the plurality of flexible cables 90, the length L1 from the sensor panel 42 to the reading IC 92 is a length corresponding to the distance between the reading circuit board 46 and the curved side 44, and the lengths L2 from the reading ICs 92 to the reading circuit board 46 are the same. Therefore, the bias of the stretching force applied to the flexible cables 90 can be reduced by the length L1 from the sensor panel 42 to the reading IC 92. Further, it is possible to attach the reading ICs 92 at the same position from one end of the flexible cable 90 connected to the reading circuit board 46 in the plurality of flexible cables 90.

The minimum value L1min of the length from the sensor panel 42 to the reading IC 92 of the flexible cable 90 is the minimum length of the wiring line connecting the sensor panel 42 and the reading IC 92. Further, the maximum value L1max of the length from the sensor panel 42 to the reading IC 92 of the flexible cable 90 is a length obtained by adding the difference ΔL between the longest distance and the shortest distance among the distances between the reading circuit board 46 and the curved side 44 to the minimum length of the wiring line connecting the sensor panel 42 and the reading IC 92. Therefore, it is possible to minimize the length L1 from the sensor panel 42 to the reading IC 92 of the flexible cable 90 as a whole. In a case in which the circuit board is the reading circuit board 46 and the reading IC 92 includes the A/D converter 93 as in this example, it is possible to minimize the concern that noise will be added to the analog signal before it is converted into a digital signal by the A/D converter 93.

The reading ICs 92 have the same performance. Therefore, it is possible to prevent unevenness in the quality of the projection image and thus the tomographic image TI caused by the difference in the performance between the reading ICs 92.

The radiation detector 21 includes the support table 52 having the attachment surface 53 which has an arc surface shape toward the opposite side of the radiation source 20 and to which the sensor panel unit 41 is attached following the arc surface shape. For example, in a case in which the sensor panel 41 has a planar shape, as represented by a broken line in FIG. 21, the irradiation dose of the radiation R in an end portion is lower than that in a central portion of the sensor panel unit 41. As a result, a scan field of view (sFOV) 1, which is an imaging range that can be reconstructed as the tomographic image TI, is reduced. On the other hand, in a case in which the sensor panel unit 41 has an arc surface shape, the entire sensor panel unit 41 is irradiated with substantially the same amount of radiation R. Therefore, a scan field of view sFOV2 can be larger than the scan field of view sFOV (sFOV2>SFOV1). For example, while sFOV1 is 384 mm, sFOV2 is 406 mm. Therefore, the sensor panel unit 41 having an arc surface shape makes it possible to image a wider range of the subject S at once.

In addition, in some CT apparatuses according to the related art, a flat sensor panel unit 41 is moved in a plane direction to obtain sFOV1. However, this CT apparatus has disadvantages that a moving mechanism for moving the sensor panel unit 41 in the plane direction is required, which results in an increase in the size of the apparatus, and it takes a long time to perform imaging. In contrast, the CT apparatus 10 according to this example does not require the moving mechanism and does not take a long time for imaging.

The sensor panel unit 41 includes two sensor panels 42A and 42B. In the sensor panels 42A and 42B, the end portions 50A and 50B on the sides 45A and 45B other than the curved sides 44A and 44B to which the reading circuit boards 46A and 46B are connected are arranged to overlap each other in the thickness direction. Therefore, the overlap portion that causes the deterioration of the quality of the tomographic image TI can be a minimum of one between the end portions 50A and 50B, and the deterioration of the quality of the tomographic image TI can be suppressed. In addition, the number of sensor panels 42 is not limited to two and may be three or more. In a case in which the number of sensor panels is increased, it is possible to image a wider range of the subject S at one time.

The reading circuit board 46A and the switching circuit board 48A connected to the sensor panel 42A and the reading circuit board 46B and the switching circuit board 48B connected to the sensor panel 42B are disposed at the positions that have a two-fold symmetrical relationship. Therefore, it is possible to maintain the weight balance of the radiation detector 21.

Figure 21:
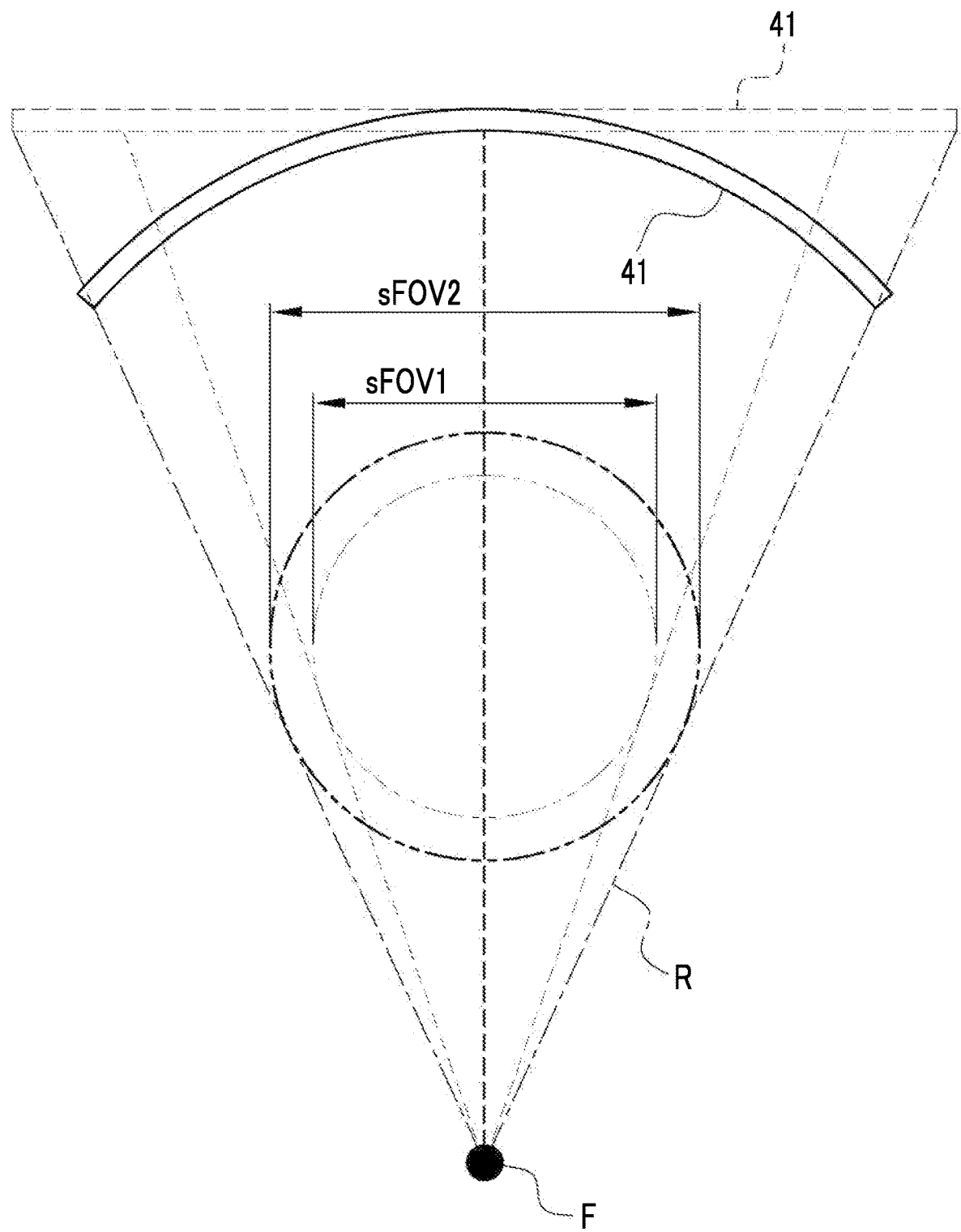
FIG. 21 is a diagram illustrating a scan field of view in a case in which the sensor panel has an arc surface shape and in a case in which the sensor panel has a planar shape.

The CT apparatus 10 comprises the annular frame 18 to which the radiation source 20 and the radiation detector 21 are attached and the rotation mechanism 120. The subject S is positioned in the cavity 19 of the frame 18. The rotation mechanism 120 rotates the frame 18 around the subject S in order to capture the projection images of the subject S at different angles. The radiation detector 21 includes the support table 52 having the attachment surface 53 which has an arc surface shape toward the opposite side of the radiation source 20 and to which the sensor panel unit 41 is attached following the arc surface shape. As illustrated in FIG. 21, the sensor panel unit 41 having an arc surface shape makes it possible to image a wider range of the subject S at one time.

As illustrated in FIG. 6, the radiation source 20 emits the radiation R with a quadrangular pyramid shape. Therefore, it is possible to complete imaging in a short time as compared to a case in which the radiation source emits the radiation R with a fan shape to perform scanning in the height direction. In addition, the radiation R having a conical shape instead of the quadrangular pyramid shape may be emitted.

As illustrated in FIGS. 1 and 5, the subject S is positioned in the cavity 19 in either the standing posture or the sitting posture. Therefore, it is possible to meet the doctor's desire to observe soft tissues, such as the lungs, in a natural state in which gravity is applied or to observe joints, such as hip joints, in a state in which gravity is applied and a load is applied.

The circuit board connected to the curved side 44 is not limited to the reading circuit board 46 described as an example. For example, as illustrated in FIG. 22, instead of the reading circuit board 46A, a switching circuit board 48A may be connected to the curved side 44A.

Figure 22:
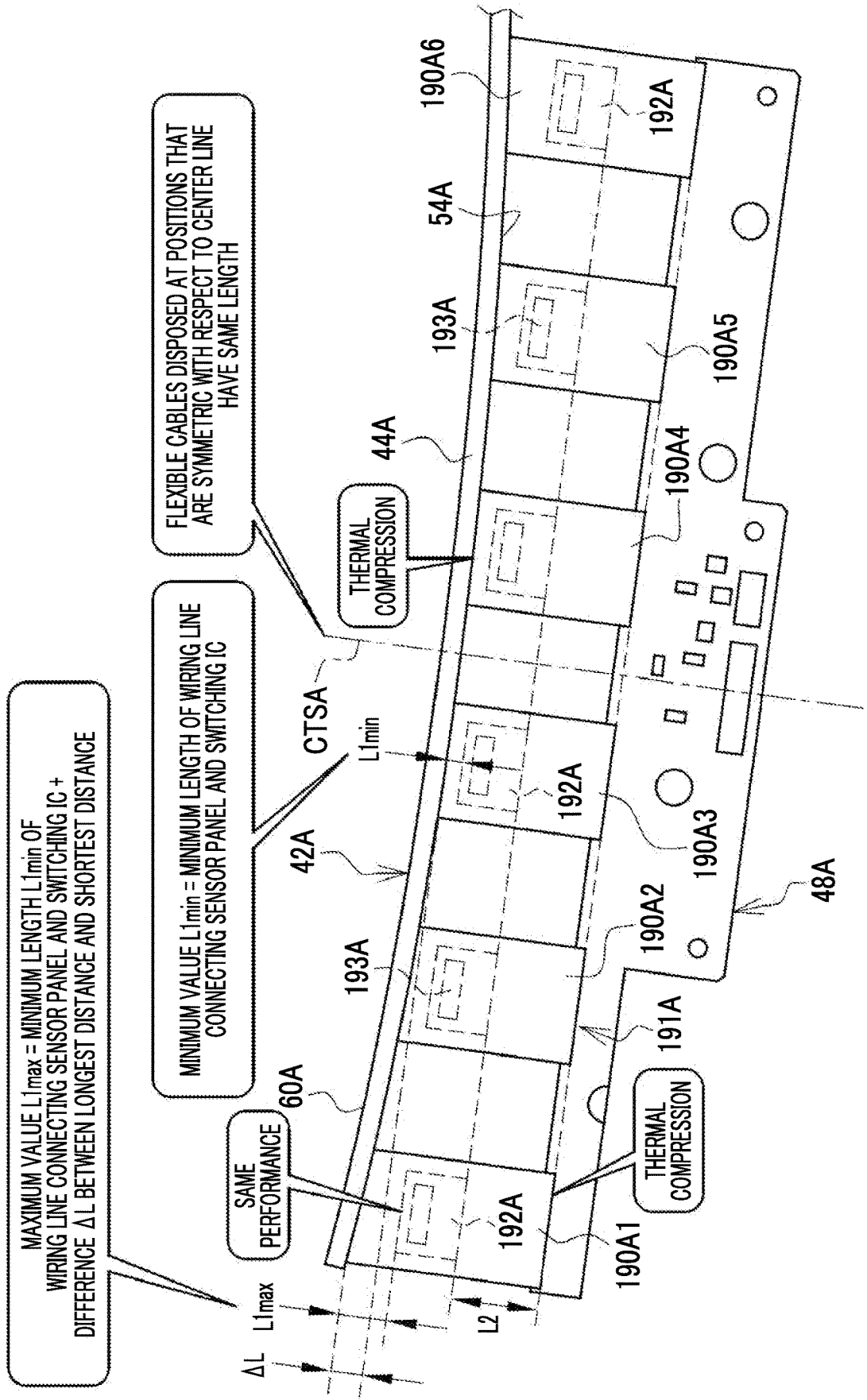
FIG. 22 is a diagram illustrating an example in which a switching circuit board is connected to the curved side instead of the reading circuit board.

In FIG. 22, the switching circuit board 48A is connected to the curved side 44A of the sensor panel 42A by flexible cables 190A1, 190A2, 190A3, 190A4, 190A5, and 190A6. The flexible cables 190A1 to 190A6 have a length corresponding to the distance between the switching circuit board 48A and the curved side 44A and constitute a reduction structure 191A.

The example illustrated in FIG. 22 has the same configuration as the example illustrated in FIG. 11 except that the switching circuit board 48A replaces the reading circuit board 46A and the flexible cables 190A1 to 190A6 replace the flexible cables 90A1 to 90A6. For example, the flexible cables 190A1 to 190A6 have one end thermally compressed to the curved side 44A before being curved and the other end thermally compressed to the switching circuit board 48A. Further, in the flexible cables 190A1 to 190A6, one end on the curved side 44A is bent toward the support table 52 in order to dispose the switching circuit board 48A toward the support table 52 at an angle of 90° with respect to the sensor panel 42A. Furthermore, the flexible cables 190A disposed at the positions that are symmetric with respect to a center line CTSA of the switching circuit board 48A, that is, the flexible cable 190A1 and the flexible cable 190A6, the flexible cable 190A2 and the flexible cable 190A5, and the flexible cable 190A3 and the flexible cable 190A4 have the same length.

A switching integrated circuit (hereinafter, abbreviated to a switching IC) 192A is mounted on each of the flexible cables 190A1 to 190A6. The switching ICs 192A have the same performance. The switching IC 192A is provided with, for example, a gate driver 193A that emits an on/off signal to be given to the TFT.

The length L1 from the sensor panel 42A to the switching IC 192A of each of the flexible cables 190A1 to 190A6 is a length corresponding to the distance between the switching circuit board 48A and the curved side 44A. On the other hand, the lengths L2 from the switching ICs 192A of the flexible cables 190A1 to 190A6 to the switching circuit board 48A are the same.

The length L1 from the sensor panel 42A to the switching IC 192A is the minimum value L1min in the flexible cables 190A3 and 190A4 disposed at the position where the distance between the switching circuit board 48A and the curved side 44A is the shortest (the length L1min is illustrated only for the flexible cable 190A3 in FIG. 22). In addition, the length L1 from the sensor panel 42A to the switching IC 192A is the maximum value L1max in the flexible cables 190A1 and 190A6 disposed at the position where the distance between the switching circuit board 48A and the curved side 44A is the longest (the length L1max is illustrated only for the flexible cable 190A1 in FIG. 22). The length L1min is the minimum length of a wiring line connecting the sensor panel 42A and the switching IC 192A. Further, the length L1max is a length obtained by adding the difference ΔL between the longest distance and the shortest distance among the distances between the switching circuit board 48A and the curved side 44A to the length L1min. The longest distance among the distances between the switching circuit board 48A and the curved side 44A is the length of the flexible cables 190A1 and 190A6 disposed at the position where the distance between the switching circuit board 48A and the curved side 44A is the longest. The shortest distance among the distances between the switching circuit board 48A and the curved side 44A is the length of the flexible cables 190A3 and 190A4 disposed at the position where the distance between the switching circuit board 48A and the curved side 44A is the shortest.

2_1st Embodiment

Figure 23:
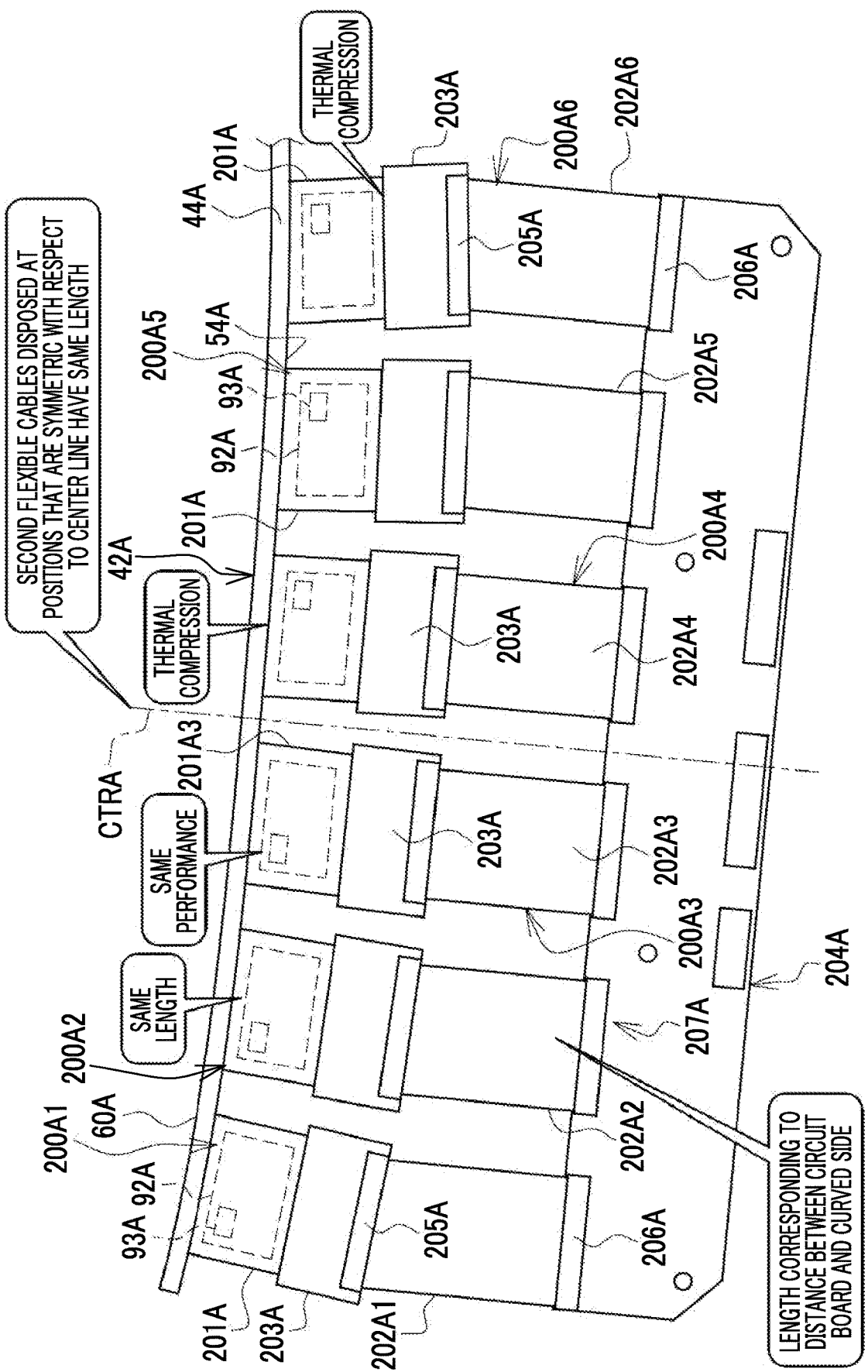
FIG. 23 is a diagram illustrating a connection structure between a sensor panel and a reading circuit board according to a 2_1st embodiment.

For example, as illustrated in FIG. 23, in a 2_1st embodiment, a plurality of flexible cables 200A1, 200A2, 200A3, 200A4, 200A5, and 200A6 are divided into first flexible cables 201A and second flexible cables 202A1, 202A2, 202A3, 202A4, 202A5, and 202A6, respectively. Therefore, relay boards 203A are disposed between the first flexible cables 201A and the second flexible cables 202A1 to 202A6.

The first flexible cable 201A has one end connected to the curved side 44A and the other end connected to the relay board 203A. One end of the first flexible cable 201A is thermally compressed to the curved side 44A. In addition, the other end of the first flexible cable 201A is also thermally compressed to the relay board 203A. The thermal compression of the first flexible cable 201A to the curved side 44A and the relay board 203A is completed before the sensor panel 42A is attached to the attachment surface 53 of the support table 52.

In the plurality of flexible cables 200A1 to 200A6, the first flexible cables 201A have the same length. In the first flexible cable 201A, one end on the curved side 44A is bent toward the support table 52 in order to dispose a reading circuit board 204A toward the support table 52 at an angle of 90° with respect to the sensor panel 42A. A reading IC 92A including, for example, an A/D converter 93A is mounted on the first flexible cable 201A. The reading ICs 92A have the same performance. In addition, the term "same" in the "same length" of the first flexible cables 201A indicates "same" including an error (for example, an error of about 1% to 10%) that is generally allowed in the technical field to which the technology of the present disclosure belongs and does not depart from the gist of the technology of the present disclosure in addition to exact "same".

In the relay board 203A, a connector 205A is provided in an end portion opposite to an end portion to which the other end of the first flexible cable 201A is thermally compressed. The other ends of the second flexible cables 202A1 to 202A6 are connected to the connectors 205A. Further, the reading circuit board 204A is provided with connectors 206A. One end of each of the second flexible cables 202A1 to 202A6 is connected to the connector 206A.

The second flexible cables 202A1 to 202A6 have a length corresponding to the distance between the reading circuit board 204A and the curved side 44A. Specifically, the second flexible cables 202A3 and 202A4 disposed at the position where the distance between the reading circuit board 204A and the curved side 44A is the shortest have the shortest length. On the other hand, the second flexible cables 202A1 and 202A6 disposed at the position where the distance between the reading circuit board 204A and the curved side 44A is the longest have the longest length. The second flexible cables 202A2 and 202A5 disposed at the position where the distance between the reading circuit board 204A and the curved side 44A is medium have a medium length. A reduction structure 207A that reduces the bias of the stretching force applied to the flexible cables 200A1 to 200A6 caused by the curved side 44A is achieved by the second flexible cables 202A1 to 202A6 having a length corresponding to the distance between the reading circuit board 204A and the curved side 44A.

The second flexible cable 202A1 and the second flexible cable 202A6 disposed at the positions that are symmetric with respect to a center line CTRA of the reading circuit board 204A have the same length. Similarly, the second flexible cable 202A2 and the second flexible cable 202A5 have the same length, and the second flexible cable 202A3 and the second flexible cable 202A4 have the same length.

As described above, in the 2_1st embodiment, each of the plurality of flexible cables 200 is divided into the first flexible cable 201 having one end connected to the curved side 44 and the second flexible cable 202 having one end connected to the reading circuit board 204. Then, in the plurality of flexible cables 200, the first flexible cables 201 have the same length. Further, each flexible cable comprises the relay board 203 to which the other end of the first flexible cable 201 and the other end of the second flexible cable 202 are connected and is disposed between the sensor panel 42 and the reading circuit board 204. Therefore, the plurality of flexible cables 200 can have the same configuration from the first flexible cable 201 to the relay board 203, and it is possible to reduce a component cost.

Since the first flexible cables 201 have the same length, the distances from the sensor panel 42 to the reading ICs 92 are the same. In a case in which the circuit board is the reading circuit board 204 and the reading IC 92 includes the A/D converter 93 as in this example, the transmission paths of the analog signals before being converted into digital signals by the A/D converter 93 have the same length. Therefore, the environment in which the analog signals are exposed can be the same in each flexible cable 200.

In the 2_1st embodiment, the reduction structure 207 is configured by the second flexible cables 202 having a length corresponding to the distance between the reading circuit board 204 and the curved side 44. A very simple configuration in which the length of the second flexible cable 202 changes depending on the distance between the reading circuit board 204 and the curved side 44 makes it possible to reduce the bias of the stretching force applied to the flexible cable 200.

The second flexible cables 202 disposed at the positions that are symmetric with respect to the center line CTR of the reading circuit board 204 have the same length. Therefore, as in the first embodiment, a variation in the length of the second flexible cable 202 can be less than that in a case in which the length of the second flexible cable 202 changes stepwise. Further, it is possible to reduce the difference ΔL between the longest distance and the shortest distance among the distances between the reading circuit board 204 and the curved side 44 and to minimize the difference between the transmission characteristics of the plurality of second flexible cables 202.

The first flexible cable 201 has one end thermally compressed to the curved side 44 before being curved and the other end thermally compressed to the relay board 203. Then, the relay board 203 has the connector 205 to which the other end of the second flexible cable 202 is connected, and the reading circuit board 204 has the connector 206 to which one end of the second flexible cable 202 is connected. Therefore, after the first flexible cable 201 is bent in a state in which the second flexible cable 202 is removed from the connector 205 of the relay board 203, the second flexible cable 202 can be connected to the connector 205. As a result, it is possible to improve workability.

Figure 24:
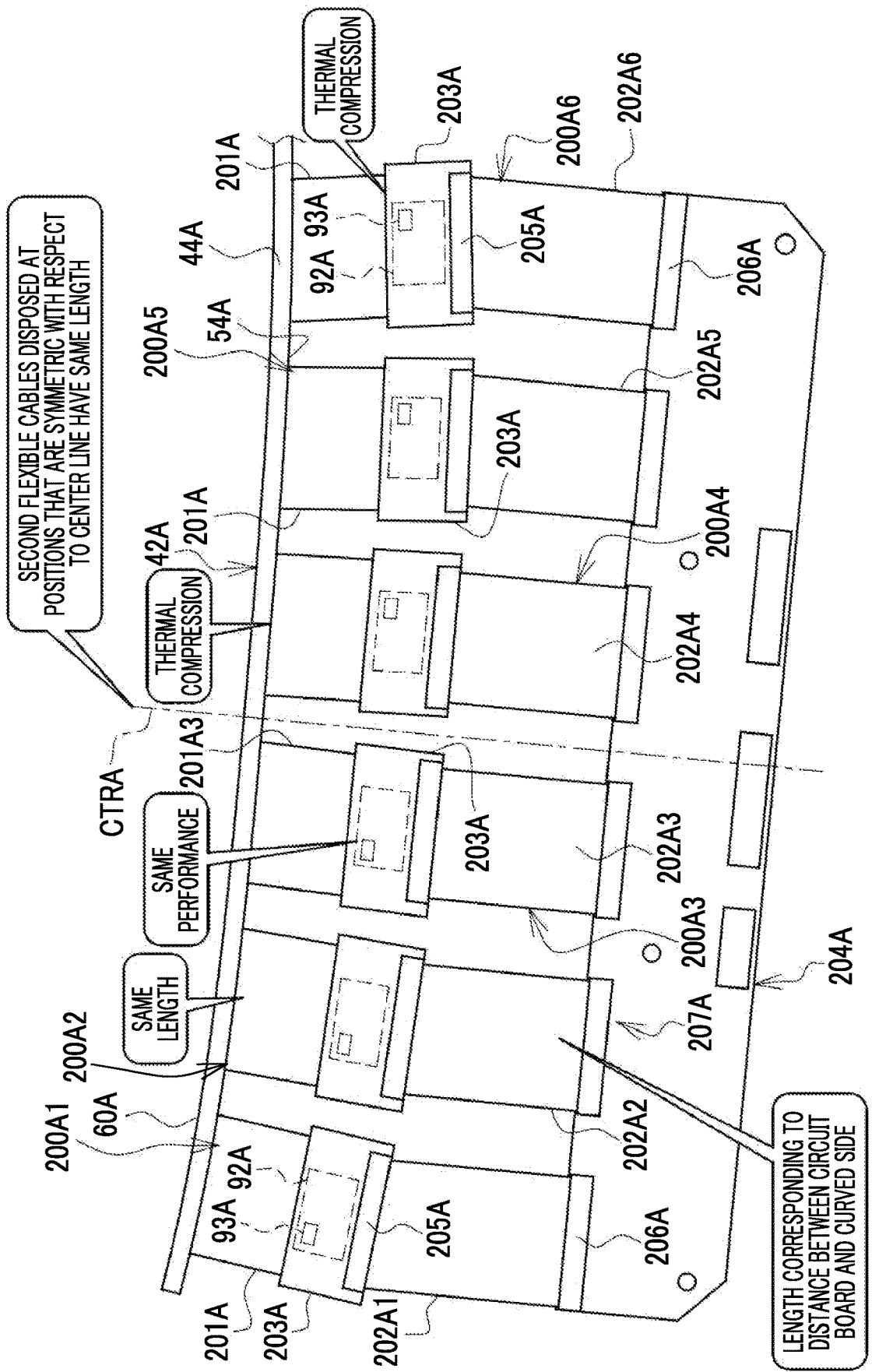
FIG. 24 is a diagram illustrating another example of the connection structure between the sensor panel and the reading circuit board according to the 2_1st embodiment.

Further, in FIG. 23, the reading IC 92 is mounted on the first flexible cable 201. However, the present disclosure is not limited thereto. For example, as illustrated in FIG. 24, the reading IC 92 may be mounted on the relay board 203. In this case, the transmission paths of the analog signals have the same length. Therefore, the environment in which the analog signals are exposed can be the same in each flexible cable 200.

Figure 25:
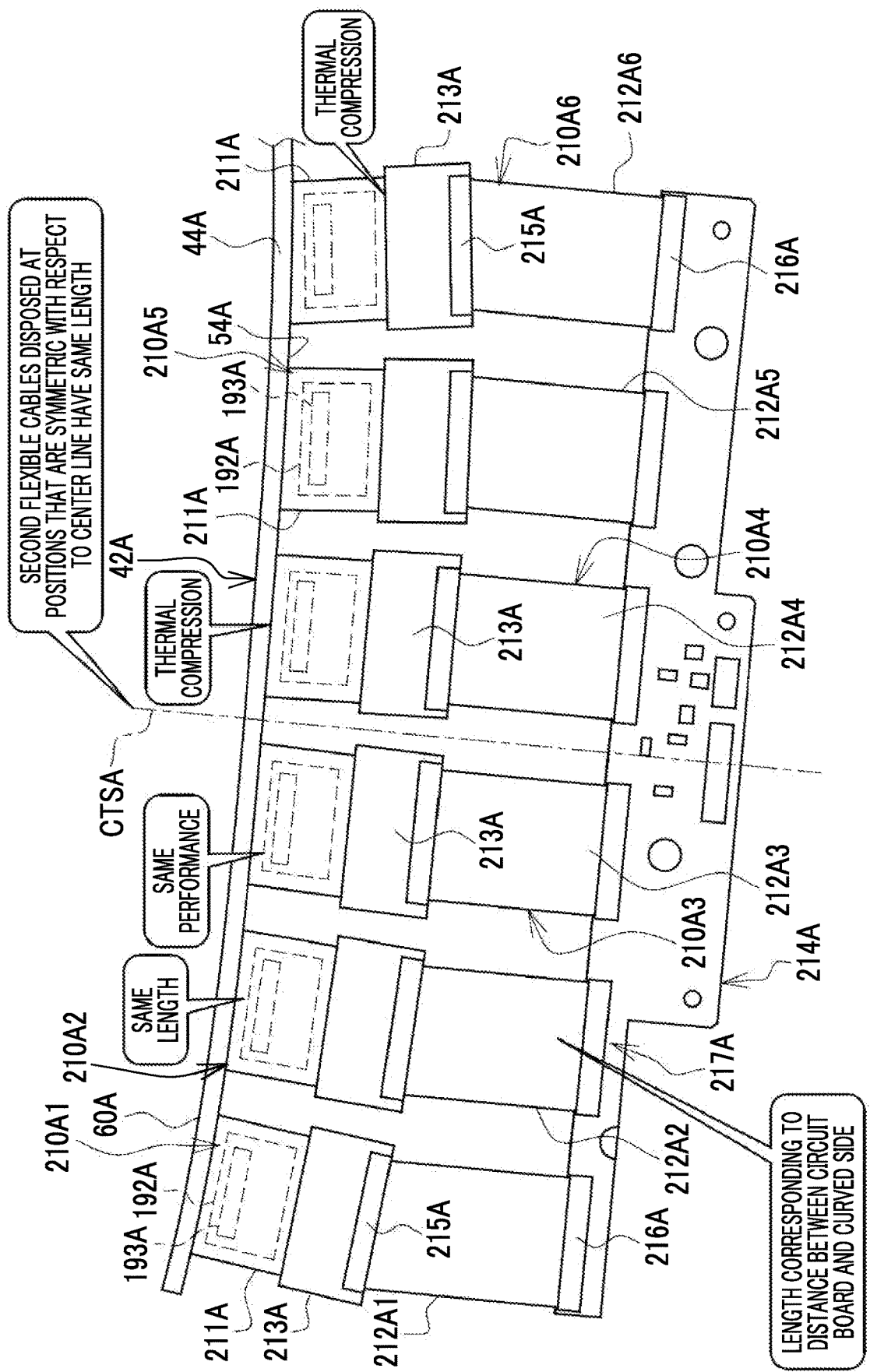
FIG. 25 is a diagram illustrating an example in which a switching circuit board is connected to the curved side instead of the reading circuit board in the 2_1st embodiment.

Further, for example, as illustrated in FIG. 25, the circuit board may be a switching circuit board 214 instead of the reading circuit board 204.

In FIG. 25, the switching circuit board 214A is connected to the curved side 44A of the sensor panel 42A by flexible cables 210A1, 210A2, 210A3, 210A4, 210A5, and 210A6. The flexible cables 210A1 to 210A6 are divided into first flexible cables 211A having one end connected to the curved side 44A and second flexible cables 212A1, 212A2, 212A3, 212A4, 212A5, and 212A6 having one end connected to the switching circuit board 214A. Then, relay boards 213A are disposed between the first flexible cables 211A and the second flexible cables 212A1 to 212A6.

One end of the first flexible cable 211A is thermally compressed to the curved side 44A before being curved. In addition, the other end of the first flexible cable 211A is also thermally compressed to the relay board 213A. In the plurality of flexible cables 210A1 to 210A6, the first flexible cables 211A have the same length. In the first flexible cable 211A, one end on the curved side 44A is bent toward the support table 52 in order to dispose the switching circuit board 214A toward the support table 52 at an angle of 90° with respect to the sensor panel 42A. A switching IC 192A including, for example, a gate driver 193A is mounted on the first flexible cable 211A.

In the relay board 213A, a connector 215A is provided in an end portion that is opposite to an end portion to which the other end of the first flexible cable 211A is thermally compressed. The other ends of the second flexible cables 212A1 to 212A6 are connected to the connectors 215A. Further, the switching circuit board 214A is provided with connectors 216A. One end of each of the second flexible cables 212A1 to 212A6 is connected to the connector 216A.

The second flexible cables 212A1 to 212A6 have a length corresponding to the distance between the switching circuit board 214A and the curved side 44A and constitute a reduction structure 217A.

The second flexible cable 212A1 and the second flexible cable 212A6 disposed at the positions that are symmetric with respect to a center line CTSA of the switching circuit board 214A have the same length. Similarly, the second flexible cable 212A2 and the second flexible cable 212A5 have the same length, and the second flexible cable 212A3 and the second flexible cable 212A4 also have the same length.

2_2nd Embodiment

Figure 26:
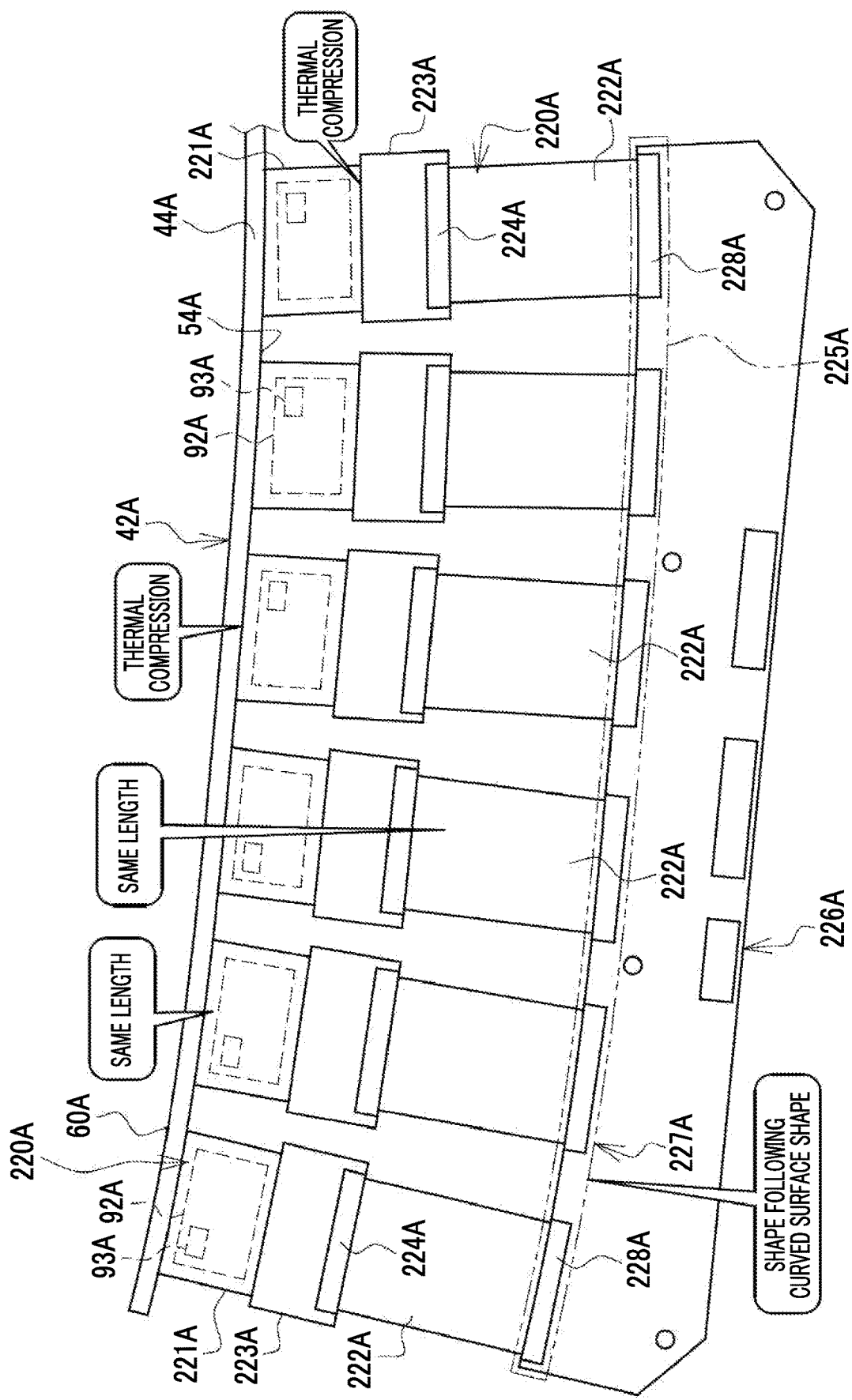
FIG. 26 is a diagram illustrating a connection structure between a sensor panel and a reading circuit board according to a 2_2nd embodiment.

For example, a 2_2nd embodiment illustrated in FIG. 26 is the same as the 2_1st embodiment in that a plurality of flexible cables 220A are divided into first flexible cables 221A and second flexible cables 222A, a relay board 223A is disposed between the first flexible cable 221A and the second flexible cable 222A, and the first flexible cables 221A have the same length. In addition, the 2_2nd embodiment is the same as the 2_1st embodiment in that the first flexible cable 221A has one end thermally compressed to the curved side 44A before being curved the other end thermally compressed to the relay board 223A and the other end of the second flexible cable 222A is connected to a connector 224A provided in the relay board 223A. Further, the 2_2nd embodiment is the same as the 2_1st embodiment in that the reading IC 92A is mounted on the first flexible cable 221A.

In the 2_2nd embodiment, in a plurality of flexible cables 220A, not only the first flexible cables 221A but also the second flexible cables 222A have the same length. Further, a reading circuit board 226A that has a curved end portion 225A having a shape following the curved side 44A is used instead of the reading circuit board 204A. The plurality of flexible cables 220A are radially extended from the curved side 44A and connected to the reading circuit board 226A. A reduction structure 227A that reduces the bias of the stretching force applied to the flexible cable 220A caused by the curved side 44A is achieved by the reading circuit board 226A having the curved end portion 225A. In addition, the term "same" in the "same length" of the second flexible cables 222A indicates "same" including an error (for example, an error of about 1% to 10%) that is generally allowed in the technical field to which the technology of the present disclosure belongs and does not depart from the gist of the technology of the present disclosure in addition to exact "same".

Connectors 228A are provided in the curved end portion 225A. One end of the second flexible cable 222A is connected to the connector 228A.

As described above, in the 2_2nd embodiment, in the plurality of flexible cables 220, the second flexible cables 222 have the same length. Then, the reduction structure 227 is configured by the reading circuit board 226 having the curved end portion 225 to which one end of the second flexible cable 222 is connected and which has a shape following the curved side 44. Therefore, the plurality of flexible cables 220 can have the same configuration, and it is possible to reduce a component cost.

In the first embodiment, in a case in which the side of the reading circuit board 46 is not straight, it takes a lot of time and effort to thermally compress the flexible cable 90. In the 2-2nd embodiment, the reading circuit board 226 has the curved end portion 225 and does not have a straight shape. However, since the reading circuit board 226 and the second flexible cables 222 are connected by the connectors 228, the problem that it takes a lot of time and effort for thermal compression does not occur.

In addition, the reading IC 92 may be mounted on the relay board 223 instead of the first flexible cable 221 in the 2_2nd embodiment, which is not illustrated. Further, this may be applied to the switching circuit board.

Third Embodiment

Figure 27:
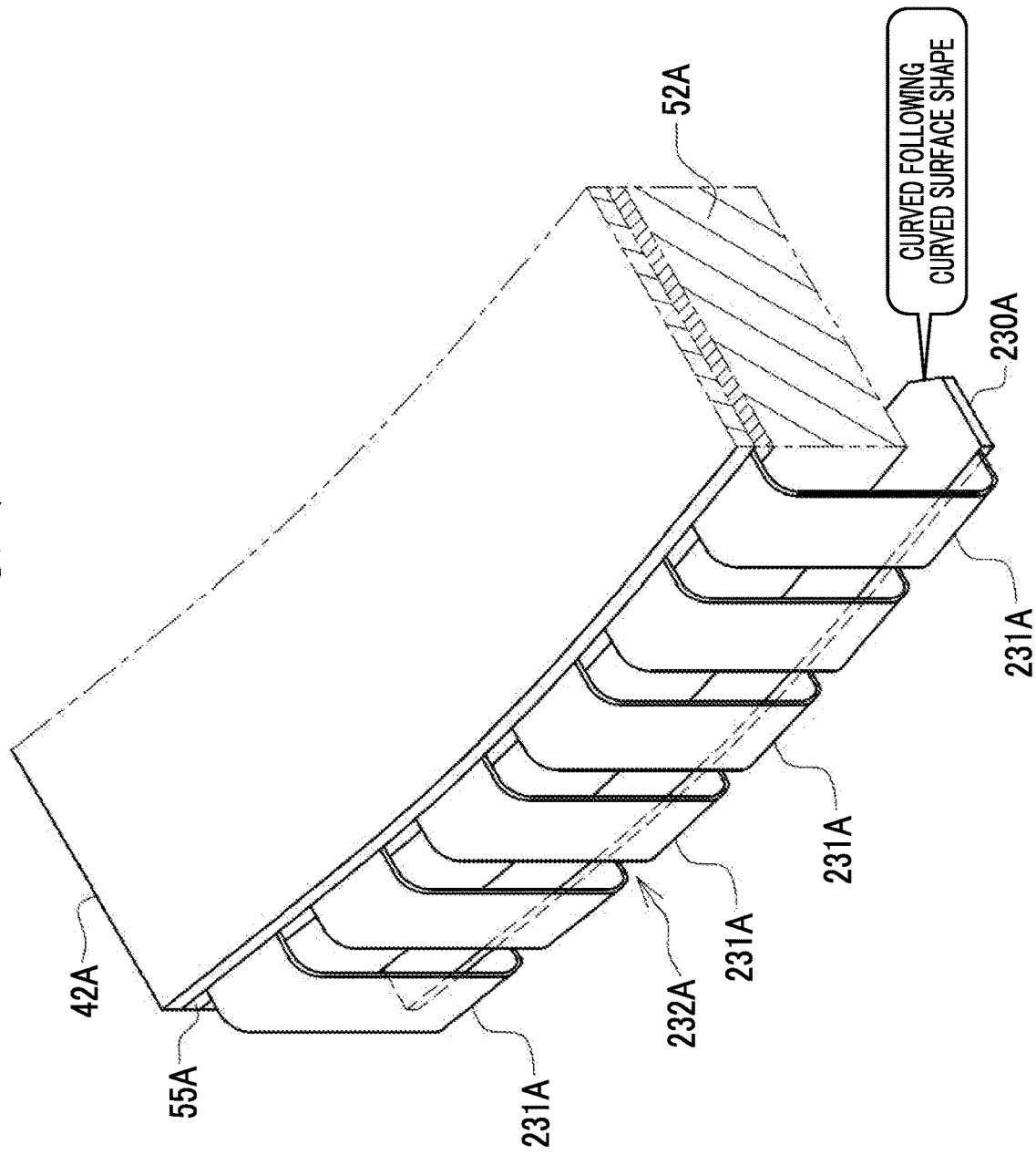
FIG. 27 is a perspective view illustrating a connection structure between a sensor panel and a reading circuit board according to a third embodiment.
Figure 28:
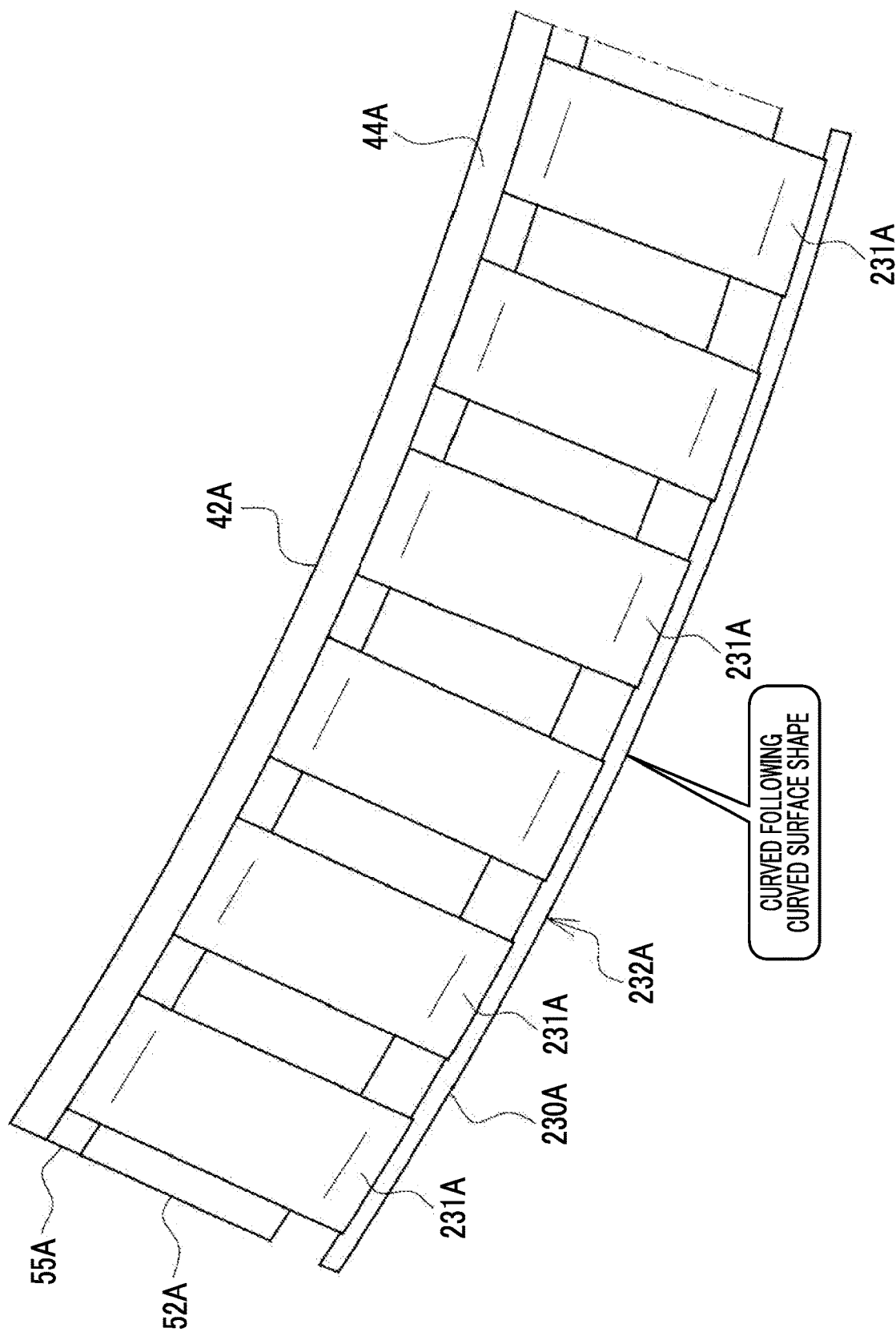
FIG. 28 is a plan view illustrating the connection structure between the sensor panel and the reading circuit board according to the third embodiment.

For example, as illustrated in FIGS. 27 and 28, in a third embodiment, the set angle is 180° and a reading circuit board 230A is disposed so as to face a surface of the support table 52 which is opposite to the attachment surface 53.

The reading circuit board 230A is connected to the curved side 44A of the sensor panel 42A by a plurality of flexible cables 231A. The flexible cables 231A have the same length. The flexible cables 231A are thermally compressed to the curved side 44A before being curved and the reading circuit board 230A. In the flexible cable 231A, one end on the curved side 44A and the other end on the side of the reading circuit board 230A are bent the support table 52 in order to dispose the reading circuit board 230A at an angle of 180° with respect to the sensor panel 42A. In addition, similarly to, for example, the above-described "90°", "180°" indicates, for example, "180°" including an error (for example, an error of about 1% to 10%) that is generally allowed in the technical field to which the technology of the present disclosure belongs and does not depart from the gist of the technology of the present disclosure, in addition to perfect "180°".

The reading circuit board 230A is formed of a flexible material made of a resin, such as polyimide, similarly to the substrate 70A of the sensor panel 42A. Therefore, the reading circuit board 230A can be curved following the arc surface shape of the sensor panel 42A. A reduction structure 232A that reduces the bias of the stretching force applied to the flexible cables 231A due to the curved side 44A is achieved by the reading circuit board 230A curved following the arc surface shape.

As described above, in the third embodiment, the reduction structure 232 is configured by the reading circuit board 230 that is curved following the arc surface shape of the sensor panel 42. Therefore, the bias of the stretching force applied to the flexible cables 231 can be reduced by a very simple configuration in which the flexible reading circuit board 230 is prepared and is then curved following the arc surface shape of the sensor panel 42. Further, the plurality of flexible cables 231 can have the same configuration, and it is possible to reduce a component cost. Furthermore, this may be applied to the switching circuit board.

Fourth Embodiment

Figure 29:
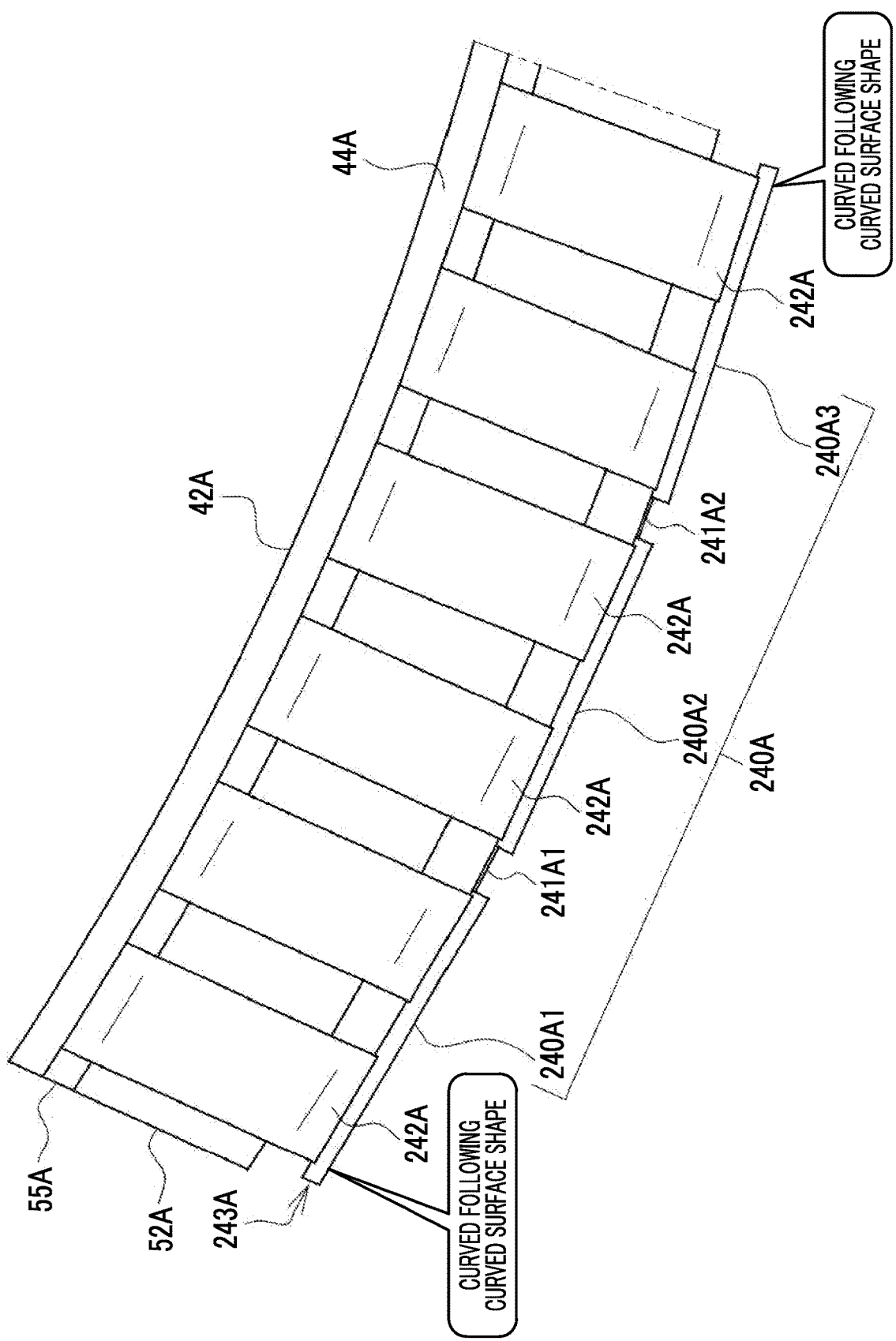
FIG. 29 is a plan view illustrating a connection structure between a sensor panel and a reading circuit board according to a fourth embodiment.

For example, as illustrated in FIG. 29, in a fourth embodiment, the set angle is 180° and a reading circuit board 240A is disposed so as to face a surface of the support table 52 which is opposite to the attachment surface 53 as in the third embodiment.

Figure 30:
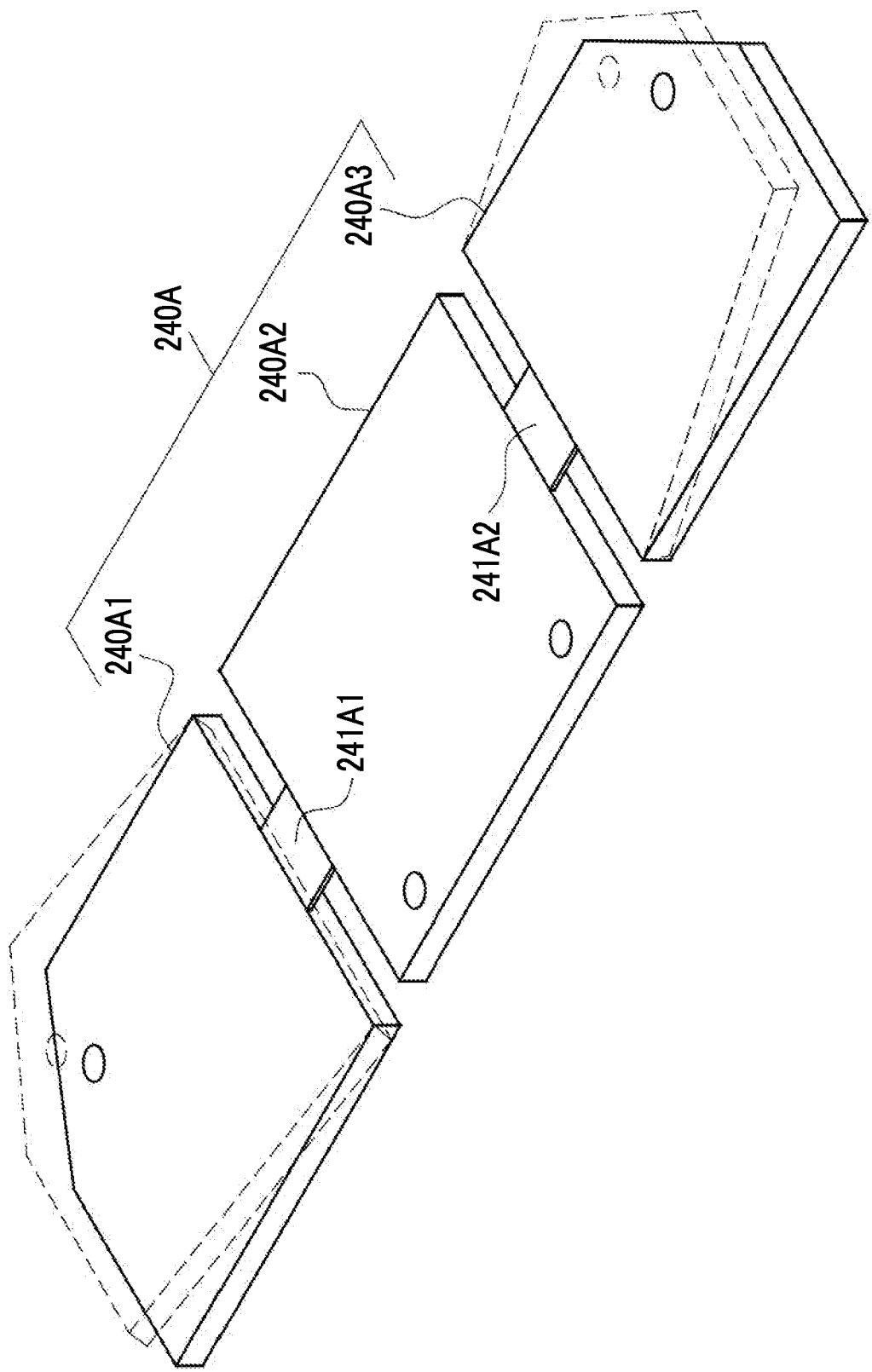
FIG. 30 is a perspective view illustrating the reading circuit board according to the fourth embodiment.

For example, as illustrated in FIG. 30, the reading circuit board 240A has a configuration in which the reading circuit board 46A according to the first embodiment is divided into three reading circuit boards 240A1, 240A2, and 240A3. The reading circuit board 240A1 and the reading circuit board 240A2 are connected by an inter-board connection flexible cable 241A1. Similarly, the reading circuit board 240A2 and the reading circuit board 240A3 are connected by an inter-board connection flexible cable 241A2. Therefore, as represented by a broken line in FIG. 30, the reading circuit board 240A1 is bent with respect to the reading circuit board 240A2 with a connection portion to the inter-board connection flexible cable 241A1 as a fulcrum. Similarly, the reading circuit board 240A3 is bent with respect to the reading circuit board 240A2 with a connection portion to the inter-board connection flexible cable 241A2 as a fulcrum.

The reading circuit board 240A is connected to the curved side 44A of the sensor panel 42A by a plurality of flexible cables 242A. The flexible cables 242A have the same length. The flexible cable 242A is thermally compressed to the curved side 44A before being curved and the reading circuit board 240A. In the flexible cable 242A, one end on the curved side 44A and the other end on the side of the reading circuit board 240A are bent toward the support table 52 in order to dispose the reading circuit board 240A at an angle of 180° with respect to the sensor panel 42A.

The reading circuit boards 240A1 and 240A3 are bent with respect to the reading circuit board 240A2 following the arc surface shape of the sensor panel 42A. A reduction structure 243A that reduces the bias of the stretching force applied to the flexible cables 242A caused by the curved side 44A is achieved by the divided reading circuit boards 240A1 to 240A3, the inter-board connection flexible cable 241A1 for connecting the reading circuit boards 240A1 and the reading circuit boards 240A2, and the inter-board connection flexible cable 241A2 for connecting the reading circuit boards 240A2 and the reading circuit boards 240A3.

Figure 31:
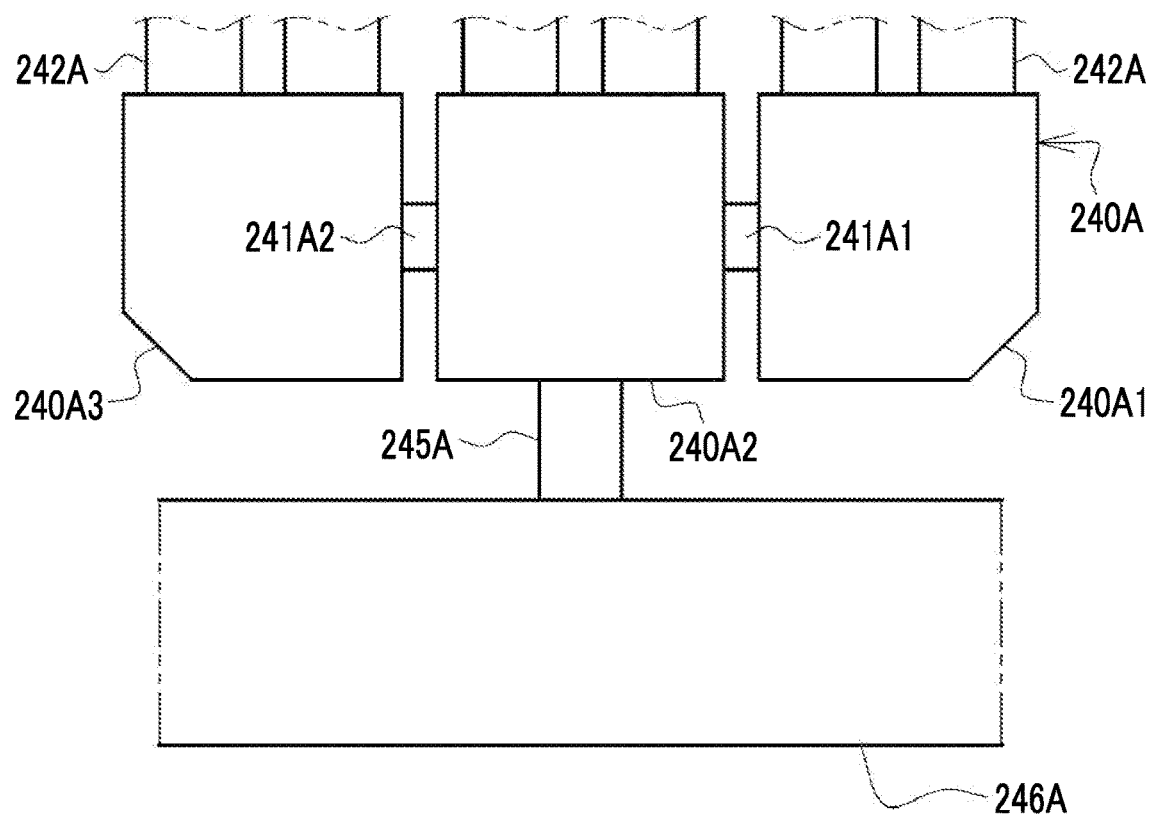
FIG. 31 is a diagram illustrating a connection aspect between divided reading circuit boards and an image processing circuit board.

For example, as illustrated in FIG. 31, in the reading circuit board 240A, the central reading circuit board 240A2 is connected to an image processing circuit board 246A in a subsequent stage by a flexible cable 245A.

As described above, in the fourth embodiment, the reduction structure 243 is configured by the divided reading circuit boards 240 and the inter-board connection flexible cables 241 for connecting the adjacent reading circuit boards 240. This configuration also makes it possible to reduce the bias of the stretching force applied to the flexible cables 242. Furthermore, this may be applied to the switching circuit board.

Figure 32:
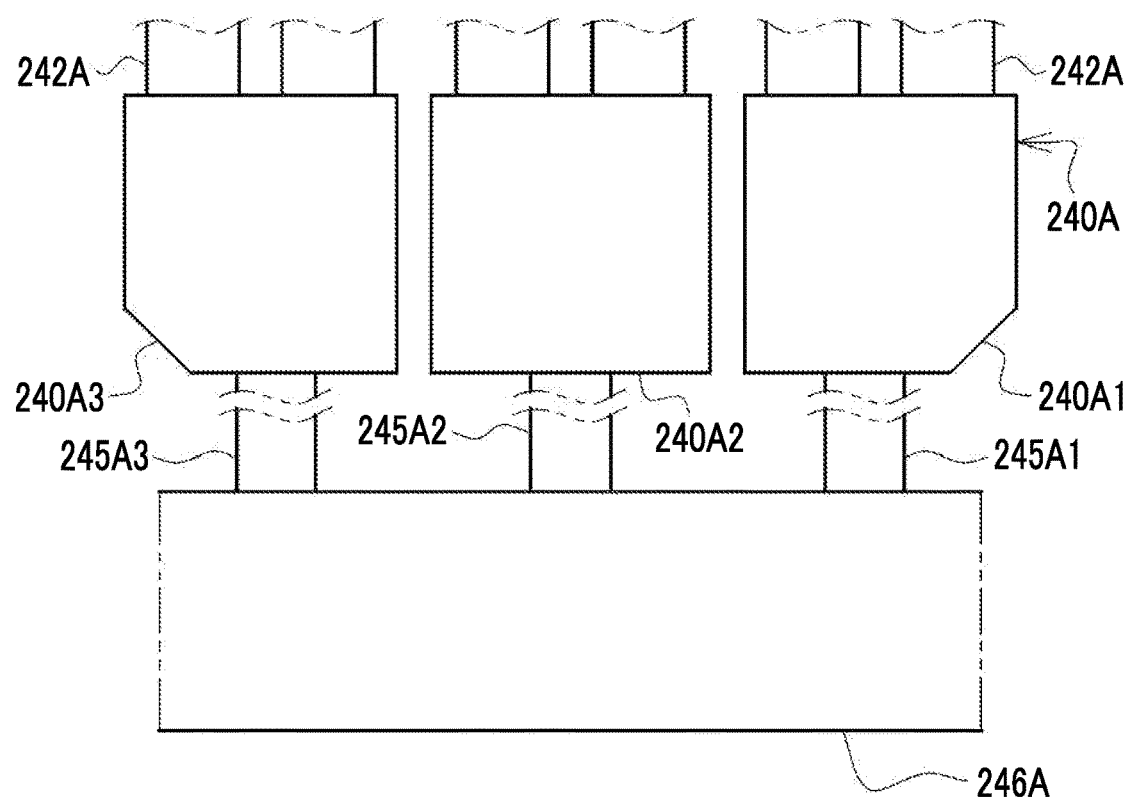
FIG. 32 is a diagram illustrating another connection aspect between the divided reading circuit boards and the image processing circuit board.

The following configuration may be used without connecting the adjacent reading circuit boards 240 with the inter-board connection flexible cable 241: the divided reading circuit boards 240 are disposed independently and connected to the image processing circuit board 246 by sufficiently long flexible cables 245 (flexible cables 245A1, 245A2, and 245A3) as illustrated in FIG. 32. This configuration also makes it possible to reduce the bias of the stretching force applied to the flexible cables 242.

Fifth Embodiment

Figure 33:
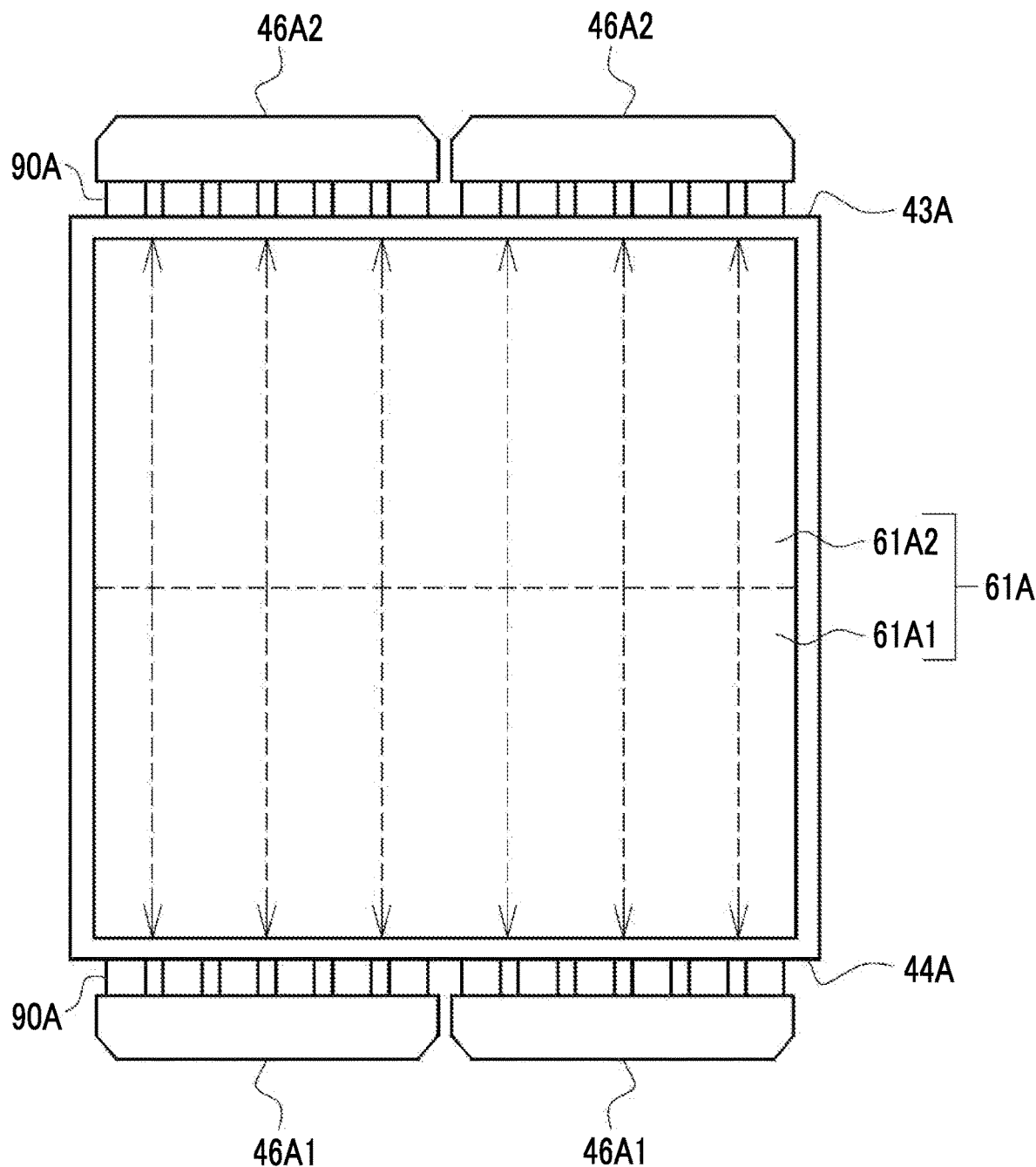
FIG. 33 is a diagram illustrating a fifth embodiment in which two reading circuit boards are connected to two opposite curved sides of a sensor panel.

For example, as illustrated in FIG. 33, in a fifth embodiment, the reading circuit board 46 is connected not only to the curved side 44 but also to the curved side 43 facing the curved side 44.

In FIG. 33, the reading circuit board 46A according to the fifth embodiment includes a first reading circuit board 46A1 that is connected to the curved side 44A through a plurality of flexible cables 90A (in FIG. 33, they are drawn with the same length to avoid complication) and a second reading circuit board 46A2 that is connected to the curved side 43A through a plurality of flexible cables 90A. The first reading circuit board 46A1 takes charge of reading out the charge of the pixels 74A in a region (hereinafter, referred to as a first imaging region) 61A1 that is half of the imaging region 61A and is close to the curved side 44A. The second reading circuit board 46A2 takes charge of reading out the charge of the pixels 74A in a region (hereinafter, referred to as a second imaging region) 61A2 that is the other half of the imaging region 61A and is close to the curved side 43A. The first reading circuit board 46A1 and the second reading circuit board 46A2 are driven independently and read out the charge at the same time. In this case, the switching circuit board 48A (not illustrated) that gives an on/off signal to the TFT of the pixel 74A in the first imaging region 61A1 and the switching circuit board 48A that gives an on/off signal to the TFT of the pixel 74A in the second imaging region 61A2 are prepared. In addition, for the reading circuit board 46B, similarly to the reading circuit board 46A, a reading circuit board which takes charge of reading out charge in a region that is half of the imaging region 61B and a reading circuit board which takes charge of reading out charge in a region that is the other half of the imaging region 61B are connected to the opposite curved sides 43B and 44B, which is not illustrated.

As described above, in the fifth embodiment, the reading circuit board 46 includes the first reading circuit board 461 that takes charge of reading out the charge in the first imaging region 611 and the second reading circuit board 462 that takes charge of reading out the charge in the second imaging region 612. Then, the first reading circuit board 461 and the second reading circuit board 462 are connected to two opposite curved sides 43 and 44 of the sensor panel 42 through the flexible cables 90. Therefore, the time required to read out the charge can be reduced by half.

The curved surface shape is not limited to the exemplified arc surface shape. The shape may be an elliptical arc surface shape or a bowl shape such as a parabolic antenna shape. In the case of the bowl shape, all of the sides of the sensor panel 42 are the curved sides. Therefore, in the first embodiment or the like, the reduction structure is applied not only to the reading circuit board 46 but also to the switching circuit board 48. Further, the frame 18 is not limited to the circular ring and may be a polygonal ring.

The example in which the rear surface of the substrate 70 is the first surface 54 has been described. However, conversely, the sensor panel 42 may be attached to the support table 52 such that the rear surface of the substrate 70 is the second surface 60.

The CT apparatus 10 is given as an example of the radiography apparatus. However, the present disclosure is not limited thereto. The radiography apparatus may be a simple radiography apparatus that captures the projection images one by one while changing the angle. Further, a radiography apparatus may be used which includes a frame to which two sets of the radiation source 20 and the radiation detector 21 are attached, simultaneously irradiates the front surface and the side surface of the subject S with the radiation R to obtain two projection images, and investigates the anatomical shape of the hip joint and spine of subject S and the connection between the spine and the lower limbs.

The hardware configuration of the computer constituting the control device 12 can be modified in various ways. For example, the control device 12 may be configured by a plurality of computers separated as hardware in order to improve processing capacity and reliability. For example, the functions of the receiving unit 145 and the RW control unit 146 and the functions of the imaging control unit 147, the image processing unit 148, and the display control unit 149 are distributed to two computers. In this case, the two computers constitute the control device 12.

As described above, the hardware configuration of the computer of the control device 12 can be appropriately changed according to required performances, such as processing capacity, safety, and reliability. Further, not only the hardware but also an application program, such as the operation program 140, may be duplicated or may be dispersively stored in a plurality of storages in order to ensure safety and reliability.

In each of the above-described embodiments, for example, the following various processors can be used as the hardware structure of processing units performing various processes, such as the receiving unit 145, the RW control unit 146, the imaging control unit 147, the image processing unit 148, and the display control unit 149. The various processors include, for example, the CPU 132 which is a general-purpose processor executing software (operation program 140) to function as various processing units, a programmable logic device (PLD), such as a field programmable gate array (FPGA), which is a processor whose circuit configuration can be changed after manufacture, and/or a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and/or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured using one or more of the various processors as the hardware structure.

In addition, specifically, an electric circuit (circuitry) obtained by combining circuit elements, such as semiconductor elements, can be used as the hardware structure of the various processors.

In the technology of the present disclosure, the above-described various embodiments and/or various modification examples may be combined with each other. In addition, the present disclosure is not limited to each of the above-described embodiments, and various configurations can be used without departing from the gist of the present disclosure. Furthermore, the technology of the present disclosure extends to a storage medium that non-temporarily stores a program, in addition to the program.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the gist of the technology of the present disclosure. In addition, in the content of the above description and illustration, the description of, for example, common technical knowledge that does not need to be particularly described to enable the implementation of the technology of the present disclosure is omitted in order to avoid confusion and facilitate the understanding of portions related to the technology of the present disclosure.

In the specification, "A and/or B" is synonymous with "at least one of A or B". That is, "A and/or B" means only A, only B, or a combination of A and B. Further, in the specification, the same concept as "A and/or B" is applied to a case in which the connection of three or more matters is expressed by "and/or".

All of the publications, the patent applications, and the technical standards described in the specification are incorporated by reference herein to the same extent as each individual document, each patent application, and each technical standard are specifically and individually stated to be incorporated by reference.

What is claimed is:

1. An x-ray radiation detector comprising:
    a support table in which an attachment surface having a curved surface shape is formed;
    a sensor panel which has a rectangular plate shape and is attached to the attachment surface while being curved following the curved surface shape and in which pixels that include thin film transistors and detect x-ray radiation are two-dimensionally arranged;
    a circuit board;
    a plurality of flexible cables that connect a curved side of the sensor panel and the circuit board, are arranged along the curved side, and are bent to dispose the circuit board at a set angle with respect to the sensor panel; and
    a reduction structure that reduces a bias of a stretching force applied to the plurality of flexible cables caused by the curved side.

2. The x-ray radiation detector according to claim 1,
    wherein the circuit board has a rectangular plate shape, and
    the reduction structure is configured by the flexible cables that have a length corresponding to a distance between the circuit board and the curved side.

3. The x-ray radiation detector according to claim 2,
    wherein each flexible cable of the plurality of flexible cables has one end thermally compressed to the curved side before being curved and the other end thermally compressed to the circuit board.

4. The x-ray radiation detector according to claim 2,
    wherein flexible cables disposed at positions that are symmetric with respect to a center line of the circuit board have the same length.

5. The x-ray radiation detector according to claim 2,
    wherein integrated circuits are respectively mounted on each flexible cable of the plurality of flexible cables.

6. The x-ray radiation detector according to claim 5,
    wherein a length from the sensor panel to the integrated circuit in the plurality of flexible cables is the length corresponding to the distance between the circuit board and the curved side, and
    lengths from the integrated circuits in the plurality of flexible cables to the circuit board are the same.

7. The x-ray radiation detector according to claim 6,
    wherein a minimum value of the length from the sensor panel to the integrated circuit of each flexible cable of the plurality of flexible cables is a minimum length of a wiring line that connects the sensor panel and the integrated circuit, and
    a maximum value of the length from the sensor panel to the integrated circuit of each flexible cable of the plurality of flexible cables is a length obtained by adding a difference between a longest distance and a shortest distance among the distances between the circuit board and the curved side to the minimum length of the wiring line connecting the sensor panel and the integrated circuit.

8. The x-ray radiation detector according to claim 5,
    wherein the integrated circuits have the same performance.

9. The x-ray radiation detector according to claim 5,
    wherein the circuit board is a reading circuit board for reading out charge accumulated in the pixel, and
    the integrated circuit includes an analog/digital converter that converts an analog signal indicated by the charge into a digital signal.

10. The x-ray radiation detector according to claim 5,
    wherein the circuit board is a switching circuit board for giving an on/off signal to each of the thin film transistors, and
    the integrated circuit includes a gate driver that emits the on/off signal.

11. The x-ray radiation detector according to claim 1,
    wherein each of the plurality of flexible cables is divided into a first flexible cable having one end connected to the curved side and a second flexible cable having one end connected to the circuit board,
    in the plurality of flexible cables, the first flexible cables have the same length, and
    the x-ray radiation detector further comprises a relay board to which another end of each first flexible cable and another end of each second flexible cable are connected and which is disposed between the sensor panel and the circuit board.

12. The x-ray radiation detector according to claim 11,
    wherein the reduction structure is configured by the second flexible cables having a length corresponding to a distance between the circuit board and the curved side.

13. The x-ray radiation detector according to claim 12,
    wherein the second flexible cables disposed at positions that are symmetric with respect to a center line of the circuit board have the same length.

14. The x-ray radiation detector according to claim 11,
    wherein, in the plurality of flexible cables, the second flexible cables have the same length, and the reduction structure is configured by the circuit board to which one end of each second flexible cable is connected and which has a curved end portion having a shape following the curved side.

15. The x-ray radiation detector according to claim 11, wherein each first flexible cable has the one end thermally compressed to the curved side and the other end thermally compressed to the relay board, the relay board has a connector to which the other end of each second flexible cable is connected, and the circuit board has a connector to which the one end of each second flexible cable is connected.

16. The x-ray radiation detector according to claim 11, wherein an integrated circuit is mounted on each first flexible cable or the relay board.

17. The x-ray radiation detector according to claim 16, wherein the circuit board is a reading circuit board for reading out charge accumulated in the pixel, and the integrated circuit includes an analog/digital converter that converts an analog signal indicated by the charge into a digital signal.

18. The x-ray radiation detector according to claim 16, wherein the circuit board is a switching circuit board for giving an on/off signal to each of the thin film transistors, and the integrated circuit includes a gate driver that emits the on/off signal.

19. The x-ray radiation detector according to claim 1, wherein the reduction structure is configured by the circuit board that is curved following the curved surface shape.

20. The x-ray radiation detector according to claim 1, wherein the reduction structure is configured by divided circuit boards and an inter-board connection flexible cable that connects adjacent circuit boards among the divided circuit boards.

21. The x-ray radiation detector according to claim 1, wherein the circuit board is a reading circuit board for reading out charge accumulated in the pixel and includes a first reading circuit board that takes charge of reading out the charge in a region which is half of the sensor panel and a second reading circuit board that takes charge of reading out the charge in a region which is the other half of the sensor panel, and the first reading circuit board and the second reading circuit board are connected to two opposite curved sides of the sensor panel through the flexible cables.

22. The x-ray radiation detector according to claim 1, wherein the sensor panel includes two sensor panels of a first sensor panel and a second sensor panel, and the first sensor panel and the second sensor panel are arranged such that end portions on sides other than the curved side to which the circuit board is connected overlap each other in a thickness direction.

23. The x-ray radiation detector according to claim 22, wherein the circuit board connected to the first sensor panel and the circuit board connected to the second sensor panel are disposed at positions that have a two-fold symmetrical relationship.

24. A radiography apparatus comprising:

the x-ray radiation detector according to claim 1; and an x-ray radiation source that emits the x-ray radiation.

25. The radiography apparatus according to claim 24, further comprising:

an annular frame to which the x-ray radiation detector and the x-ray radiation source are attached and in which a subject is positioned in a cavity; and a rotation mechanism that rotates the frame around the subject to capture radiographic images of the subject at different angles, wherein the attachment surface has an arc surface shape following the annular frame.

26. The radiography apparatus according to claim 25, wherein the radiography apparatus is a computed tomography apparatus that obtains a tomographic image of the subject on the basis of the radiographic images captured at different angles.

27. The radiography apparatus according to claim 25, wherein the x-ray radiation source emits the x-ray radiation having a conical shape.

28. The radiography apparatus according to claim 25, wherein the subject is positioned in the cavity in either a standing posture or a sitting posture.

* * * * *